United States Patent [19]

Shen

[11] Patent Number: 6,041,788

[45] Date of Patent: Mar. 28, 2000

[54] METHOD OF EVALUATING DRUG EFFECT IN A MULTIPLE DOSE CLINICAL TRIAL

[76] Inventor: Liji Shen, 102 Cherrywood Ter., Gaithersburg, Md. 20878

[21] Appl. No.: 09/225,105

[22] Filed: Jan. 4, 1999

[51] Int. Cl.[7] .................................................... A61B 19/00
[52] U.S. Cl. ............................................................. 128/898
[58] Field of Search ............................................. 128/898

[56] References Cited

U.S. PATENT DOCUMENTS

| | | | |
|---|---|---|---|
| 5,715,180 | 2/1998 | Hu ............................................ | 364/552 |
| 5,783,408 | 7/1998 | Hamilton et al. .......................... | 435/29 |
| 5,946,662 | 8/1999 | Ettl et al. ..................................... | 705/8 |

OTHER PUBLICATIONS

A.J. Sankoh et al. :"Some Comments on Frequency Used Multiple Endpoint Adjustment Methods in Clinical Trials", Statistics in Medicine, vol. 16, pp. 2529–2542, 1997.

R.B. D'Agostino et al. :"Strategies for Dealing with Multiple Treatment Comparasons in Confirmatory Clinical Trials", Drug Information Journal, vol. 27, pp. 625–641, 1993.

J.M. Lachin :"Introduction to Sample Size Determination and Power Analysis for Clinical Trials", Controlled Clinical Trials, vol. 2, pp. 93–113, 1981.

R. Makuch et al. :"Sample Size for Evaluating a Conservative Therapy", Cancer Treatment Reports, vol. 62, No. 7, pp. 1037–1040, Jul. 1978.

*Primary Examiner*—Max Hindenburg
*Assistant Examiner*—Brian Szmal

[57] ABSTRACT

The invented method is a process to evaluate drug effect in a multiple dose clinical trial. In drug development, finding an optimal dose is normally carried out by a phase II clinical trial. Then a phase III clinical trial will be conducted to demonstrate the selected dose is efficacious and safe. Because the highest observed response rate among the multiple dose groups could overestimate the true response rate of the selected dose, there is difficulty to pool the data from phase II clinical trial with the data from phase III clinical trial for final analysis. As a result, sample size of each dose group in phase II clinical trials is often underpowered to provide sufficient information for choosing an optimal dose. The invented method gives a solution to the overestimation problem. Simulations show that the invented method is better than the existing methods such as Bonferroni's procedure. The method can be used to evaluate a test drug, compare the test drug with a standard treatment, and determine an appropriate sample size when designing a clinical trial. Results of this method could support a New Drug Application and its market promotion. After all, the invented method is applicable to clinical trials in which drug effect is measured by dichotomous variables as well as continuous variables.

9 Claims, No Drawings

METHOD OF EVALUATING DRUG EFFECT IN A MULTIPLE DOSE CLINICAL TRIAL

CROSS-REFERENCE TO RELATED APPLICATIONS

None.

STATEMENT REGARDING FEDERALLY SPONSORED RESEARCH OR DEVELOPMENT

This invention is not a federally sponsored research or development.

REFERENCE TO A MICROFICHE APPENDIX

None.

BACKGROUND OF THE INVENTION

The invented method is a process to evaluate drug effect in a multiple dose clinical trial, similar to sample inspection of a product in manufacturing. In drug development, drug developers are required by federal laws to find an optimal dose and to demonstrate that the selected dose is safe and efficacious. Normally, a relatively small scaled phase II clinical trial is carried out to find a proper dose. Then an adequate and well-controlled phase III clinical trial will be conducted to confirm the results from the phase II clinical trial. In many practical situations, the number of patients in each dose group at the phase II trial can not be as large as it should be. This is because the total number of patients is the number of patients per group multiplied by the number of dose groups in the trial. A moderate increase in the number of patients in each dose group will be a substantial increase of total number of patients in the clinical trial. Drug developers can not afford both a large dose-finding clinical trial and then a large confirmatory clinical trial. If a dose-finding trial does not have an appropriate sample size, the selected dose might not be the optimal for the treatment. On the other hand, if both large phase II and phase III trials are carried out, clinical trials could be very costly and lengthy. Some useful information of drug effect in the phase II trial is wasted. Therefore, it is desired to perform a necessarily large dose-finding trial and use the data from this trial as a part of to-be-conducted phase III clinical trial for final evaluation. However, there are concerns to pool the data from dose-finding trial with the data from confirmatory trial. What has been concerned most is that the true drug effect of the selected dose might be overestimated by the highest observed response rate if a dose is determined by which dose group has the highest observed response rate. Currently, the most popular method for this problem is Bonfferroni Adjustment. But Bonfferroni Adjustment overacts when it corrects the overestimation, therefore, is known to be too conservative. The invented method improves Bonfferroni Adjustment and fills the gap between overestimating and being too conservative. As a result, clinical trials are less expensive to conduct and faster to complete. Results of the said method can also be used as evidence in the New Drug Application to be presented to the Food and Drug Administration (FDA) to seek claims for the test drug. Finally, results of the said method and the claims of the drug being supported can be used both in the labeling of the drug to educate the professionals and costumes and in advertisement to promote market shares of the drug when it completes with other drugs.

Overestimation means that an estimate is frequently greater than true value being estimated. We can use response rate as an indicator of successfulness of a dose. When we choose a dose with the highest observed response rate among dose groups, this observed response rate could overestimate true response rate of the selected dose. For example, if true response rates of dose A and dose B are the same, say 75%, then the higher of the observed rates in the two dose groups will be very likely greater than 75% due to sample variation. Then we might tend to believe that the selected dose has a response rate greater than 75%. On the other hand, this problem may not be as serious as what we have just illustrated when true response rates of competing doses are significantly different. If true response rates of dose A and dose B are 85% and 55%, respectively, dose A will almost certainly be chosen by the higher response rate in observation and the overestimation of response rate of the selected dose is unlikely a problem. But we do not know the true response rate of each dose group and the observed response rates may vary due to sample variation. This invention is a sophisticated method that decides when and how to make a correction. In practice, the FDA repeatedly requests drug developers to use Bonfferroni Adjustment to make corrections no matter what.

The paper of Sankoh, Huque and Dubey [1] is one of the best that described the problem and reviewed the existing methods. D'Agostino, Massaro, Hwan and Cabral [2] also discussed the methods to deal with multiple dose comparisons in confirmatory trials. Among various approaches, Bonfferroni's procedure is the most accepted approach because of its conservative nature. Other methods are rarely used by drug developers and thus, are not worth mentioning here. Bonfferroni's procedure raises confidence level of each comparison between a dose group and the competing drug so that the overall confidence level of comparison between the test drug and the competing drug is guaranteed. As a result, it overacts in correcting potential overestimation. Furthermore, it provides no estimate of true response rate but a significant level of statistical tests in comparison with a control group. Therefore, Bonfferroni Adjustment is not a satisfactory approach for the pharmaceutical industry in seeking a method that will appropriately correct overestimation when it is necessary.

BRIEF SUMMARY OF THE INVENTION

The said invention is a process that will provide a better estimate of true drug effect than the existing methods. It solves the problems of overestimation as well as overcorrection. It also provides a way to incorporate the information from a phase II multiple dose trial into a phase III confirmatory trial. Therefore, the dose-finding trial can be sufficiently sized to select a right dose. Comparison between the selected dose of the testing drug and a standard treatment is, in fact, a continuation of the dose finding trial. After all, design and conducting a dose-finding trial and a confirmatory trial becomes one integrated trial.

The said method is to start a clinical trial with multiple dose groups of a test drug and a control group. The control could be either a placebo or an active standard treatment. At a certain point of the trial, dose selection is performed and those unselected dose groups will be dropped. Patients after dose selection will only be enrolled to the selected dose group and the control group. The final comparison will be conducted between the selected dose group of the test drug and the control group. Data in the dose finding stage will be carried forward to the final analysis in the confirmatory stage and appropriate corrections will be made. Based on the Monte Carlo simulations, the said process can meet the FDA guideline to draw a risk/benefit conclusion within a specific statistical uncertainty.

The said method is applicable to trials of two or more doses of test drug and a control treatment in which the primarily interested drug effect is measured by rate of cure in treatment groups. When two drugs are compared, a claim that a test drug is therapeutically superior or equivalent to a standard drug is not simply based on the difference of cure rates but based on the possible range of this difference. A standard way used by pharmaceutical industry in the United States is a two-sided 95% confidence interval for the difference between the test drug and the standard treatment. The test drug could be claimed superior to the standard treatment if the lower bound of the 95% confidence interval of the difference is greater than zero. The test drug could be claimed equivalent to the standard treatment if the lower bound of the 95% confidence interval of the difference is no less than a tolerated negative amount (e.g., −15%). In other words, the claim of equivalence might be a false statement but its chance will be no more than 2.5% if true difference is −15%. If the highest observed rate without any correction is used, the actual probability of false claim (also called type I error in Statistics) will be greater than the nominal 2.5%. In contrast, Bonfferoni's procedure keeps chance of false claim well below the nominal type I error, thus, makes claims of real drug effect more difficult than we planned. The said process has the actual probability of false claim proximately the same as the nominal. Therefore, the standards that are applied conventionally in drug evaluation are also applied to this particular design of clinical trials.

The said process could also be applied to evaluate drug effect measured by a continuous variable such as reduction of fever, blood pressure, HIV viral load, etc., by adding one step to the process for assessing the homogeneity of standard deviations of drug effect in dose groups. The method could be used when the range of ratio of standard deviations is within certain limits.

The said method can also be used in planning a trial to determine how many patients are needed to keep the probability of false claim under control and the probability of true claim beyond a certain level. When an extra number of patients are added to the trial, the method can simulate the trial by adding them to the competing dose groups and/or to the remaining groups to determine the best allocation of these patients for final analysis.

DETAILED DESCRIPTION OF THE INVENTION

The process will be described in simple cases then in more complicated cases, although the principle used in all cases is the same. The first case is a clinical trial in which there are two dose groups of a test drug and one standard treatment group as a control. The clinical outcome of individuals is cure or failure. The second case deals with three dose groups. The third case is for dose groups of four and beyond. The last case could be one of the first three cases regarding to the number of doses, but the clinical outcome of individuals is measured by a continuous variable such as blood pressure, HIV rival load, etc.

Case 1:

Suppose that there are two dose groups of a test drug and one standard treatment group as a control and drug effect of individuals is cure or failure. The method for evaluating multiple dose drug effect comprises following data analyzing steps:

(a) Determining N, the number of total patients in the selected dose group at the end of trial, and $\alpha$ between 0 and 1, a proportion of N patients in each dose group enrolled by the time of dose selection. N and $\alpha$ are determined by the claims of the test drug intended to prove in the clinical trial, the power of statistical tests and feasibility to run such a trial within a reasonable budget and time frame. Some established methods in reference [3] and [4] can be used to determine the initial values of N and $\alpha$.

(b) Selecting a dose of the test drug at the time when $\alpha N$ patients per dose group finish their treatment and are ready for evaluation. Let $\hat{p}_1$, and $\hat{p}_2$ be the proportions of cure in Dose 1 group and Dose 2 group by that time. Dose 1 will be selected if $\hat{p}_1 \geq \hat{p}_2$; otherwise, Dose 2 will be selected. The maximum of two observed cure rates, $\hat{p}_s = \max(\hat{p}_1, \hat{p}_2)$, will be used as an estimate of true cure rate of the selected dose group, $p_s$. That is, $p_s = p_i$ if $\hat{p}_s = \hat{p}_i$, $i=1,2$.

(c) Estimating the bias of $\hat{p}_s - p_s$, the difference of the estimated cure rate and true cure rate of the selected dose group. As we have pointed out that $p_s$ is likely overestimated by $\hat{p}_s$. The average of overestimation, or called the bias, is estimated by $\hat{b}_{12}(\gamma)$, Stepwise Overcorrection subject to a tuning parameter $\gamma$ in $(0, \infty)$. The method is noted as SOC($\gamma$) in abbreviation. The recommended $\gamma$ is 2 or around based on Monte Carlo simulations.

$$\hat{b}_{12}(\gamma) = \sqrt{(\hat{\sigma}_1^2 + \hat{\sigma}_2^2)/(2\pi)} \, e^{-((i-1)\gamma)^2/2}, \text{ when} \qquad (1)$$

$$(\hat{p}_1, \hat{p}_2, \hat{\sigma}_1^2, \sigma_2^2) \in A_i, i = 1, 2, \ldots$$

where $$A_i = \left\{ (\hat{p}_1, \hat{p}_2, \hat{\sigma}_1^2, \hat{\sigma}_2^2) \,\Big|\, (i-1)\gamma \leq |\hat{p}_1 - \hat{p}_2|/\sqrt{\hat{\sigma}_1^2 + \hat{\sigma}_2^2} < i\gamma \right\}.$$

and $\hat{\sigma}_1^2 = \hat{p}_1(1-\hat{p}_1)/\alpha N$, $\hat{\sigma}_2^2 = \hat{p}_2(1-\hat{p}_2)/\alpha N$.

(d) Estimating the variance of $\hat{p}_s - p_s$, the difference of the estimated cure rate and the true cure rate of the selected dose group by $\hat{\sigma}_T^2$, which is $$\hat{\sigma}_T^2 = \hat{\sigma}_1^2 \Phi(0, \hat{p}_2 - \hat{p}_1, \hat{\sigma}_1^2 + \hat{\sigma}_2^2) + \hat{\sigma}_2^2 \Phi(0, \hat{p}_1 - \hat{p}_2, \hat{\sigma}_1^2 + \hat{\sigma}_2^2) + \qquad (2)$$

$$\frac{(\hat{p}_1 - \hat{p}_2)(\hat{\sigma}_2^2 - \hat{\sigma}_1^2)}{\sqrt{2\pi(\hat{\sigma}_1^2 + \hat{\sigma}_2^2)}} e^{-\frac{(\hat{p}_1-\hat{p}_2)^2}{2(\hat{\sigma}_1^2+\hat{\sigma}_2^2)}} - \frac{(\hat{\sigma}_2^2 + \hat{\sigma}_1^2)}{2\pi} e^{-\frac{(\hat{p}_1-\hat{p}_2)^2}{(\hat{\sigma}_1^2+\hat{\sigma}_2^2)}}$$

wherein $\Phi(\bullet, \mu, \sigma^2)$ is a normal distribution function.

(e) Enrolling $(1-\alpha)N$ patients per group in the selected dose group and the control group if $\alpha$ 1, calculating the proportion of cure in the selected dose group from dose selection to the end of clinical trial, $\hat{p}_{aft}$, and estimating the variance of the estimated cure rate of the selected dose group by $\hat{\sigma}_{aft}^2 =$ $$\hat{\sigma}_{aft}^2 = \hat{p}_{aft}(1-\hat{p}_{aft})/(1-\alpha)N \qquad (3)$$

(f) Estimating the cure rate of the control group by $\hat{p}_c$, the proportion of cures of the total patients in the control group, and estimating the variance of the estimated cure rate in the control group by $\hat{\sigma}_c^2 = \hat{p}_c(1-\hat{p}_c)/N$.

(g) Constructing an estimate for the cure rate of the selected dose by $$\hat{p}_1 \alpha \hat{p}_s(1-\alpha) \, \hat{p}_{aft} - \alpha \hat{b}_{12}(\gamma), \qquad (5),$$

and an estimate for the variance of $\hat{p}_1$ by $\alpha^2 \hat{\sigma}_T^2 + (1-\alpha)^2 \hat{\sigma}_{aft}^2$.

(h) Constructing a two-sided 95% confidence interval for the difference of cure rates between the selected dose of the test drug and the standard treatment $$95\% \ C.I. = \hat{p}_t - \hat{p}_c \pm 1.96\sqrt{\alpha^2 \hat{\sigma}_T^2 + (1-\alpha)^2 \hat{\sigma}_{aft}^2 + \hat{\sigma}_c^2} \quad (6)$$

(i) Performing a statistical test as to show that the test drug is better than the standard treatment, and surrendering the significance of difference called p value, $$p=1-\Phi(\hat{d}, 0, 1)+\Phi(-\hat{d}, 0, 1), \quad (7),$$

and $$\hat{d} = (\hat{p}_t - \hat{p}_c) / \sqrt{\alpha^2 \hat{\sigma}_T^2 + (1-\alpha)^2 \hat{\sigma}_{aft}^2 + \hat{\sigma}_c^2} \quad (8)$$

Application of above data analyzing procedure includes (1) Designing and conducting a clinical trial featured with step (a) to (i), which particularly includes using the method in the Investigational New Drug, the protocol of a clinical trial.
(2) Documenting the results of step (a) to (i) in the New Drug Application when the trial is completed, and submitting the results to the FDA as evidence to support claims of the test drug.
(3) Using the results of step (a) to (i) in the labeling of the test drug.
(4) Using the results of step (a) to (i) in the advertisement of the test drug.

EXAMPLE 1

Pharmaceutical Company ABC decided to develop a new drug called X for the treatment of tuberculosis. There were two doses of this drug that looked promising. Dose 1 was 4 mg/kg once daily for 180 days and dose 2 was 2 mg/kg twice daily for 180 days. The standard treatment on market was Drug Y whose dose was 3 mg/kg twice daily for 180 days. Company ABC believed that Drug X would be at least as good as Drug Y. Drug was evaluated by cure rate. The Company determined that 175 patients per group would be enrolled to the trial and a dose of Drug X would be selected when the first one-third of 175 patients in each group completed their treatment. By the time of dose selection, the cure rates of Dose 1 and Dose 2 were 86.4% and 66.1%, respectively. Thus, only group of Dose 1 was continued to compare with Drug Y. At the end of the trial, the estimates of cure rates of Dose 1 of Drug X and Drug Y were 77.0% and 74.9% using step (b) to (g). The 95% confidence interval of the difference in cure rates was (−6.8%, 11.0%) according to step (h). The Company reported the results to the FDA in the New Drug Application and claimed that Drug X in Dose 1 has a 77% cure rate and it is therapeutically equivalent to Drug Y. The new method supported the claims by showing that, with 95% confidence, Drug X taken 4 mg/kg once daily for 180 days would not be worse than Drug Y by 6.8% of cure rate. The lower bound of confidence interval for Bonfferroni Adjustment will be −7.9%, which adds a little bit more uncertainty of equivalence in assessment. Similar statements could be used in labeling and advertisement of Drug X.

Rationale of the method

Assume that the true response rates of Dose 1, Dose 2 and the control are $p_1$, $p_2$, and $p_c$, respectively. The proportions of cure in Dose 1 and Dose 2, $\hat{p}_1$ and $\hat{p}_2$, are centered at $p_1$ and $P_2$, and deviate from them obeying normal distributions, i.e., $\hat{p}_1 \sim N(p_1, \sigma_1^2)$ and $\hat{p}_2 \sim N(p_2, \sigma_2^2)$, where $\sigma_1^2 = p_1(1-p_1)/\alpha N$, $\sigma_2^2 = p_2(1-p_2)/\alpha N$. The maximum of observed cure rates, $\hat{p}_s = \max(\hat{p}_1, \hat{p}_2)$, is used to estimate the true rate of the selected dose, $p_s$. Closeness of $\hat{p}_s$ and $p_s$ is characterized by the probability distribution of the difference between them. The difference of $\hat{p}_s - p_s$ is of a probability density function f(t) as shown in Appendix A.

$$f(t)=\phi(t+p_1, p_1, \sigma_1^2)\Phi(t+p_1, p_2, \sigma_2^2)\phi(t+p_2, p_2, \sigma_2^2)\Phi(t+p_2, p_1, \sigma_1^2),$$

where $\phi(\cdot, \mu, \sigma^2)$ and $\Phi(\cdot, \mu, \sigma^2)$ are a normal density function and a normal distribution function. Numerical calculation under various $p_1$ and $p_2$ shows that f(t) can be approximately replaced by a normal density function which has the same mean and variance of $\hat{p}_s - p_s$. This discovery forms the basis of said method. The mean and variance of $\hat{p}_s - p_s$ are derived in Appendix B. An estimate of the mean is given in step (c). An estimate of variance of $\hat{p}_s - p\hat{s}$ is given in (d). The data of dose finding stage are integrated with confirmatory stage in step (e) to (i). Through a typical situation of drug development in the following paragraphs, we will show in Monte Carlo simulations that overestimation is corrected.

Assume that we try to demonstrate that the selected dose group is therapeutically equivalent to a standard drug. The equivalence rule is that the lower bound of two-sided 95% confidence interval of the difference of cure rates between the test drug and the standard drug is above −15%. Sample size is 175 per group and dose selection will take place when the first quarter of 175 patients in each group completed the trial. A desired method is such that the probability of equivalence will no more than 2.5% when true cure rate of the standard treatment is 15% better than the selected dose of the test drug, meanwhile that the probability to claim equivalence will be as high as possible when true cure rate of the standard treatment is the same as the selected dose of the test drug.

Three methods are compared, Max Response, the said invention (SOC), and Bonfferroni Adjustment. Max Response indicates a method in which the best observed cure rate of test drug is used directly to compare with the standard drug without consideration of bias caused by multiple dose groups of the test drug. Bonfferroni Adjustment in this case is an approach to demonstrate the equivalence by a two-sided 97.5% confidence interval instead of the two-sided 95% confidence interval for the difference of cure rates. Let $\hat{p}_u$ be an estimate of true cure rate of the selected dose without correction. Then $\hat{p}_u = \alpha\hat{p}_s + (1-\alpha)\hat{p}_{aft}$. Let $\hat{\sigma}_u^2 = \hat{p}_u(1-\hat{p}_u)/N$ be the estimate of variance of $\hat{p}_u$. Remember that $\hat{p}_1$ is the estimate of cure rate of the selected dose in step (g). Then, the confidence intervals for the difference of two drugs in cure rates are Max Response: $\hat{p}_u - \hat{p}_c \pm 1.96 \sqrt{\hat{\sigma}_u^2 + \hat{\sigma}_c^2}$, SOC: $\hat{p}_t - \hat{p}_c \pm 1.96 \sqrt{\alpha^2 \hat{\sigma}_T^2 + (1-\alpha)^2 \hat{\sigma}_{aft}^2 + \hat{\sigma}_c^2}$, Bonfferroni Adjustment: $\hat{p}_u - \hat{p}_c \pm 2.24 \sqrt{\hat{\sigma}_u^2 + \hat{\sigma}_c^2}$.

Table 1 shows that for a trial of only one dose to test, the probability of equivalence is 2.5% as tolerated when the cure rate of the standard treatment is 65% and the cure rate of the test drug is only 50%. Meanwhile the probability of equivalence is 78.9% when both true cure rates of the standard treatment and the test drug are 50%. When a trial has two doses of the test drug, overestimation likely occurs and equivalence is easier to be claimed if there is no proper adjustment. Table 1 shows that the probability of equivalence for Max Response is 3.8%, therefore, exceeding 2.5%, when true cure rate of the standard treatment is 65% and 50% for the test drug. False equivalence by Max Response when true cure rate of the standard treatment is 60% is also concerned as a probability of 20.8% compared to 15.7% in one-dose trial. Although the probability of equivalence is as high as 85.4% for Max Response when true cure rate of standard treatment is equal to the test drug, Max Response is not an acceptable method because it inflates chance of false equivalence beyond the nominal amount. The said invention, SOC($\gamma$), is also shown in Table 1, where the tuning parameter, $\gamma$, varies from 0 to 3. When $\gamma=2$, the probability of equivalence of SOC($\gamma=2$) is the tolerated 2.5% when true response rate of the standard treatment is 15% higher than that of the selected dose. The probability of equivalence of SOC($\gamma=2$) is 81.9% when true cure rates of the standard treatment and the selected dose are both 50%. The probability of equivalence of SOC($\gamma=2$) is 15.8% when $p_c=0.60$, which is close to 15.7%, the probability of equivalence if a trial had one dose of the test drug for comparison. The probability of equivalence of SOC($\gamma=2$) is 48.5% when $p_c=0.55$. This probability looks high but acceptable because true cure rate of the standard treatment is only 5% better than the cure rate of the test drug. Bonfferroni Adjustment has lower probabilities of equivalence across-the-board than former methods. Therefore, it is regarded as a conservative approach. Table 2 will show that Bonfferroni Adjustment is less ideal regarding the power of methods to prove equivalence when only one dose of the test drug has the same cure rate as the standard treatment and other doses are inferior to the standard treatment. This property of Bonfferroni Adjustment is particularly true when more than two doses of the test drug are to be investigated in a clinical trial.

TABLE 1-continued

Probability of accepting equivalence of two doses[1] ($\gamma$ = 0,1,2,3)

| Response rate of each group | $p_c = 0.5$ | $p_c = 0.55$ | $p_c = 0.60$ | $p_c = 0.65$ |
|---|---|---|---|---|
| Bonfferroni Adjustment | 0.788 | 0.440 | 0.131 | 0.018 |

[1]Results are based on 100000 simulations of 175 subjects in each group and dose selection takes place at the first quarter of patients in each group.

In Table 2, the ability of methods to demonstrate equivalence is compared when one dose of test drug has the same cure rate as the standard drug and another dose of test drug falls behind. Bonfferroni Adjustment has the lowest power to claim the equivalence of the selected dose of the test drug to the standard treatment. The said invention, SOC($\gamma$), is better than Bonfferroni Adjustment but less powerful than Max Response. Because Max Response cannot satisfy the nominal tolerance of false equivalence as explained earlier, it is not appropriate to be used for evaluating drugs. SOC($\gamma=2$) increases the power by 3% compared to Bonfferroni Adjustment in Table 2. However, both of them are less powerful than the situation when only one dose of the test drug is compared with the standard treatment and it has exact same cure rate as the standard treatment. This is largely due to the assumption that the right dose of test drug in one-dose trial has been selected while SOC and Bonfferroni Adjustment in a two-dose trial still have to choose a dose and it is possible to select a wrong dose to compare with the standard treatment. Therefore, the power of one-dose design as shown in Table 2 is not achievable for a two-dose trial under the same sample size.

TABLE 2

Power of methods of two dose design when $\gamma$ =0,1,2,3[1]

| | One-dose design | | | | | |
|---|---|---|---|---|---|---|
| Without continuity | $p_c = p = 0.5$ 0.789 | $p_c = p = 0.6$ 0.822 | $p_c = p = 0.7$ 0.869 | $p_c = p = 0.75$ 0.905 | $p_c = p = 0.8$ 0.947 | $p_c = p = 0.9$ 0.998 |
| | Two-dose design | | | | | |
| | $p_c = p_1 = 0.5$ $p_2 = 0.5$ | $p_c = p_1 = 0.6$ $p_2 = 0.5$ | $p_c = p_1 = 0.7$ $p_2 = 0.5$ | $p_c = p_1 = 0.75$ $p_2 = 0.5$ | $p_c = p_1 = 0.8$ $p_2 = 0.5$ | $p_c = p_1 = 0.9$ $p_2 = 0.5$ |
| Max Resp. | 0.856 | 0.731 | 0.842 | 0.894 | 0.938 | 0.996 |
| SOC($\gamma$ = 0) | 0.827 | 0.699 | 0.829 | 0.886 | 0.935 | 0.996 |
| SOC($\gamma$ = 1) | 0.820 | 0.691 | 0.820 | 0.879 | 0.931 | 0.996 |
| SOC($\gamma$ = 2) | 0.819 | 0.682 | 0.811 | 0.871 | 0.928 | 0.996 |
| SOC($\gamma$ = 3) | 0.819 | 0.677 | 0.800 | 0.858 | 0.917 | 0.995 |
| Bonfferro. | 0.788 | 0.648 | 0.776 | 0.836 | 0.897 | 0.991 |

[1]Results are based on 100000 simulations of the first quarter of 175 subjects for dose selection and 175 patients per remaining group for final analysis.

TABLE 1

Probability of accepting equivalence of two doses[1] ($\gamma$ = 0,1,2,3)

| Response rate of each group | $p_c = 0.5$ | $p_c = 0.55$ | $p_c = 0.60$ | $p_c = 0.65$ |
|---|---|---|---|---|
| p = 0.5 (one dose design) $p_1 = 0.5, p_2 = 0.5$ | 0.789 | 0.456 | 0.157 | 0.025 |
| Max Response | 0.854 | 0.549 | 0.208 | 0.038 |
| SOC($\gamma$ = 0) | 0.827 | 0.499 | 0.170 | 0.029 |
| SOC($\gamma$ = 1) | 0.820 | 0.488 | 0.162 | 0.027 |
| SOC($\gamma$ = 2) | 0.819 | 0.485 | 0.158 | 0.025 |
| SOC($\gamma$ = 3) | 0.819 | 0.484 | 0.156 | 0.023 |

The ability of a method to demonstrate equivalence in a two-dose trial depends on possibility of a dose to be selected and whether the selected dose is equivalent to the standard treatment. The expected power at best is the weighted sum of probabilities of every dose claimed to be equivalent to the standard treatment. The weight is the probability of each dose to be selected. The probability of selecting dose A rather than dose B is $1-\Phi(0, p_1-p_2, \sigma_1^2+\sigma_2^2)$. The first two rows in Table 3 are probabilities of equivalence when test drug is equivalent or inferior to the standard treatment. The expected power of a two-dose trial in Table 3 is the weighted sum of two rows. The expected power is a little higher than the power of SOC($\gamma=2$). But the power of Bonfferroni Adjustment is further lower than the expected power. Room for improvement of the power of SOC is limited. If the power of SOC is not satisfied, one should consider increasing the number of patients for final comparison and/or for dose selection. In other words, N and/or α should be increased.

TABLE 3

Expected powers for a two-dose trial

One-dose design

| | $p_c = p = 0.5$ | $p_c = p = 0.6$ | $p_c = p = 0.7$ | $p_c = p = 0.75$ | $p_c = p = 0.8$ | $p_c = p = 0.9$ |
|---|---|---|---|---|---|---|
| Equivalence is true | 0.789 | 0.822 | 0.869 | 0.905 | 0.947 | 0.998 |
| Test dose is poor, p = 0.5 | $P_c = 0.5$ 0.789 | $p_c = 0.6$ 0.153 | $p_c = 0.7$ 0.002 | $P_c = 0.75$ 0.000 | $P_c = 0.8$ 0.000 | $P_c = 0.9$ 0.000 |

Two-dose design[1]

| | $p_c = p_1 = 0.5$ $p_2 = 0.5$ | $p_c = p_1 = 0.6$ $p_2 = 0.5$ | $p_c = p_1 = 0.7$ $p_2 = 0.5$ | $p_c = p_1 = 0.75$ $p_2 = 0.5$ | $p_c = p_1 = 0.8$ $p_2 = 0.5$ | $p_c = p_1 = 0.9$ $p_2 = 0.5$ |
|---|---|---|---|---|---|---|
| Expected | 0.789 | 0.680 | 0.846 | 0.900 | 0.946 | 0.998 |
| SOC(γ = 2) | 0.819 | 0.682 | 0.811 | 0.871 | 0.928 | 0.996 |
| Bonfferro. | 0.788 | 0.648 | 0.776 | 0.836 | 0.897 | 0.991 |

[1]Dose selection takes place when the first quarter of 175 subjects in each group completed the trial.

Application to design a two-dose trial

If the power of said method is not satisfied, one should increase sample size. Assume that additional 100 patients will be enrolled in the trial. There are many ways to allocate these patients. We use three topical allocations of these patients to show how the simulations as displayed in Table 1 and Table 2 can be used as a means to achieve the best power of the method under the given sample size. The first allocation is to use these 100 patients for dose selection, i.e., to keep N equal to 175 and to increase α to 0.82. The second allocation is to use 50 patients of them for dose selection and 25 patients each for the remaining two groups of the selected dose and the standard treatment, i.e., to increase N to 200 and α to 0.47. The third allocation is to add all 100 patients to the remaining groups after dose selection, i.e., to increase N to 225 and relatively lower α to 0.194 from 0.25. The simulations of these three allocations are displayed in Table 4 and Table 5.

TABLE 4

Comparison of probability of equivalence of two doses[1] (γ = 1.5, 1.75, 2)

| $p_1 = 0.5, p_2 = 0.5$ | $p_c = 0.5$ | $P_c = 0.55$ | $P_c = 0.60$ | $p_c = 0.65$ |
|---|---|---|---|---|
| Allocation 1 | | | | |
| SOC(1.5) | 0.846 | 0.510 | 0.171 | 0.025 |
| SOC(1.75) | 0.844 | 0.504 | 0.165 | 0.024 |
| SOC(2) | 0.843 | 0.500 | 0.160 | 0.023 |
| Bonfferroni Adjustment | 0.847 | 0.506 | 0.161 | 0.021 |
| Allocation 2 | | | | |
| SOC(1.5) | 0.878 | 0.550 | 0.182 | 0.026 |
| SOC(1.75) | 0.878 | 0.549 | 0.182 | 0.026 |
| SOC(2) | 0.877 | 0.545 | 0.179 | 0.025 |
| Bonfferroni Adjustment | 0.858 | 0.509 | 0.154 | 0.020 |

TABLE 4-continued

Comparison of probability of equivalence of two doses[1] (γ = 1.5, 1.75, 2)

| $p_1 = 0.5, p_2 = 0.5$ | $p_c = 0.5$ | $P_c = 0.55$ | $P_c = 0.60$ | $p_c = 0.65$ |
|---|---|---|---|---|
| Allocation 3 | | | | |
| SOC(1.5) | 0.902 | 0.588 | 0.196 | 0.025 |
| SOC(1.75) | 0.900 | 0.585 | 0.194 | 0.024 |
| SOC(2) | 0.900 | 0.584 | 0.193 | 0.024 |
| Bonfferroni Adjustment | 0.881 | 0.543 | 0.167 | 0.018 |

[1]Results in the table are based on 100000 simulations.

Table 4 shows that the false equivalence of SOC is slightly higher than Bonfferroni Adjustment when standard treatment has higher cure rate than the test drug. However, it is still acceptable. The choice of γ for SOC in a range of 1.5 to 2 is not very sensitive to the probability of false equivalence. As we can see in Table 5, it is not sensitive for the power of the method within each allocation either when only one dose of the test drug is equivalent to the standard drug. SOC demonstrates itself to be more powerful than Bonfferroni Adjustment in all three different allocations of these 100 patients. The power of SOC in Allocation 1 is the lowest among the three allocations. While power of SOC in Allocation 3 is higher than in Allocation 2 when $p_c$, $p_1$ are greater than or equal to 0.7, and $p_2$=0.5, it reverses when one dose of the test drug is equivalent to the standard treatment and others are slightly below the standard treatment. For example, when $p_c$=$p_1$=0.6 and $p_2$=0.5, powers of SOC(2) are 0.787 in Allocation 2 and 0.759 in Allocation 3. To enhance the power to demonstrate true equivalence in cases that cure rates of the test doses are close and only one dose is possibly equivalent to the standard treatment, Allocation 2 should be used in conducting a successful trial.

TABLE 5

Comparison of power of methods
in two-dose design when γ = 1.5,1.75,2[1]

|  | $p_c = p_1 = 0.6$ $p_2 = 0.5$ | $p_c = p_1 = 0.7$ $p_2 = 0.5$ | $p_c = p_1 = 0.75$ $p_2 = 0.5$ | $p_c = p_1 = 0.8$ $p_2 = 0.5$ | $p_c = p_1 = 0.9$ $p_2 = 0.5$ |
|---|---|---|---|---|---|
| Allocation 1 | | | | | |
| SOC(1.5) | 0.755 | 0.850 | 0.897 | 0.938 | 0.996 |
| SOC(1.75) | 0.747 | 0.847 | 0.896 | 0.937 | 0.996 |
| SOC(2) | 0.742 | 0.846 | 0.895 | 0.937 | 0.996 |
| Bonfferroni | 0.728 | 0.794 | 0.841 | 0.897 | 0.991 |
| Allocation 2 | | | | | |
| SOC(1.5) | 0.792 | 0.889 | 0.927 | 0.962 | 0.998 |
| SOC(1.75) | 0.792 | 0.888 | 0.926 | 0.961 | 0.998 |
| SOC(2) | 0.787 | 0.885 | 0.926 | 0.961 | 0.998 |
| Bonfferroni | 0.767 | 0.851 | 0.890 | 0.934 | 0.996 |
| Allocation 3 | | | | | |
| SOC(1.5) | 0.762 | 0.898 | 0.943 | 0.974 | 0.999 |
| SOC(1.75) | 0.760 | 0.896 | 0.942 | 0.974 | 0.999 |
| SOC(2) | 0.759 | 0.894 | 0.941 | 0.973 | 0.999 |
| Bonfferroni | 0.733 | 0.870 | 0.919 | 0.958 | 0.999 |

[1]Results in the table are based on 100000 simulations.

Above example illustrates a process for allocating patients in the treatment groups and choosing a proper tuning parameter in order to achieve the designed probability of false claim and to maximize the power of said method. Sample size and its allocation can also be determined by this Monte Carlo approach as we add more patients to the trial till proper power of the method for true claims is realized. The method comprises steps:

(a) Determining the initial number of patients and calculating the probability of false claim and the power of the method using Monte Carlo simulation.

(b) If power of the method is not satisfactory, increasing the proportion of patients per group for dose selection and simulating probability of false claim and power of the method till power of the method will not increase significantly.

(c) If power of the method is still not satisfactory, increasing the number of patients in the remaining groups after dose selection, simulating probability of false claim and power of the method till power of the method will not increase significantly.

(d) Comparing the probabilities of false claim and the powers of the method to determine a tuning parameter γ for the method. Choice of γ is to achieve the designed probability of false claim and maximize the power of said method.

Summary

The said invention comprises steps to estimate cure rate of the selected dose for the test drug and to compare it with the standard treatment. It also demonstrates ways to simulate the probability of false claim and power of the method when designing a clinical trial. The simulations can be used to determine adequacy of sample size and suitability of tuning parameter γ. In all circumstances, the method is better than Bonfferroni Adjustment in the sense of higher powers to support a true claim while keeping the false claim under the control.

Case 2

Suppose that there are three dose groups of a test drug and one standard treatment group as a control and the clinical outcome of individuals is cure or failure. The method for evaluating multiple dose drug effect comprises following data analyzing steps:

(a) Same as Case 1(a).

(b) Selecting a dose of the test drug that shows the best cure rate by the time when αN patients per group finish their treatment and are ready for evaluation, i.e., $\hat{p}_s$ = max($\hat{p}_1, \hat{p}_2, \hat{p}_3$), as an estimate of true cure rate of the selected dose group, $p_s$.

(c) Estimating the bias of $\hat{p}_s - p_s$, the difference of the estimated cure rate and true cure rate of the selected dose group, by $\hat{b}_{SOC}(\gamma)$, $\hat{b}_{SOC}(\gamma) = \hat{b}_{12}\Phi(0,$ $\hat{p}_3 - \hat{p}_{12},$ $\hat{\sigma}_3^2 + \hat{\sigma}_{12}^2) +$ $\hat{b}_{23}\Phi(0, \hat{p}_1 -$ $\hat{p}_{23}, \hat{\sigma}_1^2 + \hat{\sigma}_{23}^2) +$ $\hat{b}_{31}\Phi(0, \hat{p}_2 - \hat{p}_{31},$ $\hat{\sigma}_2^2 + \hat{\sigma}_{31}^2)$ (9)

wherein $\hat{b}_{ij}$ is in the formula of Case 1(c), $\hat{p}_{ij} = (\hat{p}_i\hat{\sigma}_j^2 + \hat{p}_j\hat{\sigma}_i^2)/(\hat{\sigma}_j^2 + \hat{\sigma}_i^2)$ and $\hat{\sigma}_{ij}^2 = \hat{\sigma}_i^2\hat{\sigma}_j^2/(\hat{\sigma}_i^2 + \hat{\sigma}_j^2)$ (d) Estimating the variance of, by $\sigma_T^2$, the variance of the estimated density function of Appendix A, $$\hat{\sigma}_T^2 = \int_{-\infty}^{+\infty} t^2 \hat{f}(t)dt - \left(\int_{-\infty}^{+\infty} t\hat{f}(t)dt\right)^2 \quad (10)$$

(e) Same as Case 1(e).

(f) Same as Case 1(f).

(g) Same as Case 1(g).

(h) Same as Case 1(h).

(i) Same as Case 1(i).

The applications are the same as presented in Case 1.

Rationale of method

The rationale in Case 2 is almost the same as in Case 1. The probability density function of $\hat{p}_s - p_s$ can be approximated by a normal density function with the mean and the variance of $\hat{p}_s - p_s$. The mean is calculated in Appendix C and the estimate of this mean is constructed in step (c) of Case 2. Comparison of SOC($\gamma$) and other methods is based on Monte Carlo simulation. The example that will be used here is still to demonstrate therapeutical equivalence of a test drug and the standard treatment by excluding the selected dose of the test drug is more than 15% lower in cure rate than the standard treatment. The conclusion in Table 6 is that the probability of false equivalence of Max Response is higher than allowed, the probability of false equivalence of Bonfferroni Adjustment is lower than allowed, and SOC($\gamma$=2) has the exact level of false equivalence tolerated. The confidence interval of Bonfferroni Adjustment used in this case is adjusted by the number of doses of the test drug.

Max Response: $\hat{p}_u - \hat{p}_c \pm 1.96\sqrt{\hat{\sigma}_u^2 + \hat{\sigma}_c^2}$, SOC: $\hat{p}_t - \hat{p}_c \pm 1.96\sqrt{\alpha^2 \hat{\sigma}_T^2 + (1-\alpha)^2 \hat{\sigma}_{aft}^2 + \hat{\sigma}_c^2}$, Bonfferroni Adjustment: $\hat{p}_u - \hat{p}_c \pm 2.39\sqrt{\hat{\sigma}_u^2 + \hat{\sigma}_c^2}$.

TABLE 6

Probability of accepting equivalence in three dose design ($\gamma$ = 0,1,2,3)

| Response rate of each group | $p_c$ = 0.5 | $p_c$ = 0.55 | $P_c$ = 0.60 | $p_c$ = 0.65 |
|---|---|---|---|---|
| p = 0.5 (one dose design) | 0.787 | 0.452 | 0.157 | 0.025 |
| $p_1 = p_2 = p_3 = 0.5$ Two stage[1] | | | | |
| Max Response | 0.878 | 0.594 | 0.240 | 0.047 |
| SOC($\gamma$ = 0) | 0.836 | 0.515 | 0.183 | 0.032 |
| SOC($\gamma$ = 1) | 0.824 | 0.496 | 0.170 | 0.028 |
| SOC($\gamma$ = 2) | 0.818 | 0.483 | 0.160 | 0.025 |
| SOC($\gamma$ = 3) | 0.816 | 0.478 | 0.156 | 0.024 |
| Bonfferroni Adjustment | 0.764 | 0.412 | 0.125 | 0.017 |

[1]Two stage means dose selection takes place at the first quarter of 175 patients per group from 100000 simulations.

SOC($\gamma$=2) also leads in the ability to show equivalence when one dose of the test drug has the same cure rate as the standard drug and other two doses are less effective in cure rate. The probability to demonstrate equivalence of SOC(2) could be as much as 6% higher than Bonfferroni Adjustment as shown in Table 7.

TABLE 7

Power of methods in three dose design when doses have different response rates[1]

| | One-dose design | | | | | |
|---|---|---|---|---|---|---|
| Without continuity | $p_c$ = p = 0.5 | $p_c$ = p = 0.6 | $p_c$ = p = 0.7 | $p_c$ = p = 0.75 | $p_c$ = $p_1$ = 0.8 | $p_c$ = p = 0.9 |
| | 0.791 | 0.820 | 0.869 | 0.904 | 0.947 | 0.997 |

| | Two-stage[2], three-dose design | | | | | |
|---|---|---|---|---|---|---|
| | $p_c$ = $p_1$ = 0.5 | $p_c$ = $p_1$ = 0.6 | $p_c$ = $p_1$ = 0.7 | $p_c$ = $p_1$ = 0.75 | $p_c$ = $p_1$ = 0.8 | $p_c$ = $p_1$ = 0.9 |
| | $p_{2,3}$ = 0.5 | $p_{2,3}$ = 0.5 | $p_{2,3}$ = 0.5 | $p_{2,3}$ = 0.5 | $p_{2,3}$ = 0.5 | $p_{2,3}$ = 0.5 |
| Max Resp. | 0.881 | 0.676 | 0.825 | 0.896 | 0.936 | 0.995 |
| SOC($\gamma$ = 0) | 0.840 | 0.626 | 0.801 | 0.885 | 0.930 | 0.995 |
| SOC($\gamma$ = 1) | 0.829 | 0.614 | 0.786 | 0.875 | 0.928 | 0.995 |
| SOC($\gamma$ = 2) | 0.824 | 0.600 | 0.771 | 0.865 | 0.921 | 0.995 |
| SOC($\gamma$ = 3) | 0.822 | 0.594 | 0.748 | 0.841 | 0.903 | 0.993 |
| Bonfferro. | 0.760 | 0.555 | 0.713 | 0.807 | 0.872 | 0.987 |

[1]Results in the table are based on 25000 simulations of 175 subjects in each group.
[2]Two stage means dose selection takes place at the first quarter of total sample.

Same procedure could be employed to design a three-dose trial for appropriate sample size and allocation.

Case 3

Suppose that there are four dose groups of a test drug and one standard treatment group as a control and the clinical outcome of individuals is cure or failure. The method for evaluating multiple dose drug effect comprises following data analyzing steps:

(a) Same as Case 1(a).

(b) Selecting a dose of the test drug that shows the best cure rate by the time when $\alpha N$ patients per group finish their treatment and are ready for evaluation, i.e., $\hat{p}_s$ = max($\hat{p}_1, \hat{p}_2, \hat{p}_3, \hat{p}_4$), as an estimate of true cure rate of the selected dose group, $p_s$: $p_s = p_i$, if $\hat{p}_i = \hat{p}_s$.

(c) Estimating the bias of the difference of the estimated cure rate and true cure rate of the selected dose group, $\hat{p}_s - p_s$, by $\hat{b}_{SOC}(\gamma)$.

$$\hat{b}_{SOC}(\gamma) = \sum_{i \neq j \neq k \neq l} \hat{b}_{ij} \hat{P}(i, j, k, l) \quad (11)$$

in which $\hat{b}_{ij}$, is in the formula of Case 1(c) and $$\hat{P}(i, j, k, l) = \int_{-\infty}^{+\infty} \varphi(u, \hat{p}_{ij}, \hat{\sigma}_{ij}^2) \Phi(u, \hat{p}_k, \hat{\sigma}_k^2) \Phi(u, \hat{p}_l, \hat{\sigma}_l^2) du,$$

$$\hat{p}_{ij} = (\hat{\sigma}_i^2 \hat{p}_j + \hat{\sigma}_j^2 \hat{p}_i)/(\hat{\sigma}_i^2 + \hat{\sigma}_j^2) \text{ and } \hat{\sigma}_{ij}^2 = \hat{\sigma}_i^2 \hat{\sigma}_j^2 /(\hat{\sigma}_i^2 + \hat{\sigma}_j^2).$$

(d) Estimating the variance of $\hat{p}_s - p_s$ by $\hat{\sigma}_T^2$, $$\hat{\sigma}_T^2 = \int_{-\infty}^{+\infty} t^2 \hat{f}(t) dt - \left( \int_{-\infty}^{+\infty} t \hat{f}(t) dt \right)^2 \quad (12)$$

which can be obtained by the variance of the estimated density function in Appendix A, $$\hat{f}(t) = \sum_{i=1}^{4} \varphi(t + \hat{p}_i, \hat{p}_i, \hat{\sigma}_i^2) \prod_{j \neq i} \Phi(t + \hat{p}_i, \hat{p}_j, \hat{\sigma}_j^2).$$

(e) Same as Case 1(e).
(f) Same as Case 1(f).
(g) Same as Case 1(g).
(h) Same as Case 1(h).
(i) Same as Case 1(i).

The same applications as presented in Case 1.

Rationale of method

The rationale in Case 3 is almost the same as in Case 1. The probability density function of $\hat{p}_s - p_s$ is approximated by a normal density function with the same mean and variance of $\hat{p}_s - p_s$. The mean can be obtained in Appendix C and its estimate is given in step (c) of Case 3. Comparison of SOC($\gamma$) and other methods will still be based on Monte Carlo simulation. The example used here is to demonstrate equivalence of a test drug and the standard treatment by excluding the selected dose of the test drug is more than 15% lower in cure rate than the standard treatment. Table 8 shows that the probability of false equivalence is higher than the allowed for Max Response and lower than the allowed for Bonfferroni Adjustment. SOC fills the gap between Max Response and Bonfferroni Adjustment. Particularly, SOC($\gamma$= 2) has the acceptable tolerance for false equivalence. The confidence interval of Bonfferroni Adjustment is adjusted by the number of doses of the test drug, i.e., a two-sided 99.375% confidence interval.

TABLE 8

Probability of accepting equivalence in four dose design ($\gamma$ = 0,1,2,3)[2]

| Response rate of each group | $p_c = 0.5$ | $p_c = 0.55$ | $P_c = 0.60$ | $p_c = 0.65$ |
|---|---|---|---|---|
| p = 0.5 (one dose design) | 0.796 | 0.457 | 0.153 | 0.024 |
| $p_1 = p_2 = p_3 = p_4 = 0.5$ Two stage[1] | | | | |
| Max Response | 0.898 | 0.625 | 0.261 | 0.052 |
| SOC($\gamma$ = 0) | 0.849 | 0.529 | 0.186 | 0.031 |
| SOC($\gamma$ = 1) | 0.841 | 0.512 | 0.173 | 0.026 |
| SOC($\gamma$ = 2) | 0.828 | 0.492 | 0.162 | 0.025 |
| SOC($\gamma$ = 3) | 0.825 | 0.485 | 0.158 | 0.023 |
| Bonfferroni Adjustment | 0.756 | 0.396 | 0.112 | 0.013 |

[1]Two stage means dose selection takes place at the first quarter of 175 patients per group.
[2]The results of this table were based on 20000 Simulations.

Regarding to the power of methods, SOC definitely has higher probabilities to demonstrate equivalence than Bonfferroni Adjustment when at least one dose of the test drug is equivalent to the standard treatment. In Table 9, the power of SOC(2) is 83.3% compared to 75.5% for Bonfferroni Adjustment when all doses have the same cure rate as the standard treatment. The power of SOC(2) keeps approximately 0.06 above the power of Bonfferroni Adjustment when one dose of the test drug is equivalent to the standard treatment and the other doses are inferior. In summary, Max Response inflates the probability of false equivalence as demonstrated in Table 8. Bonfferroni Adjustment keeps the probability of false equivalence well below the tolerated level but it is under-powered for demonstrating true equivalence. SOC, when an appropriate tuning parameter is chosen, has the tolerated false equivalence and higher power for true equivalence than Bonfferroni Adjustment.

TABLE 9

Power of tests in four dose design when doses have different response rates[1]

One-dose design

| | $P_c = p = 0.5$ | $p_c = p = 0.6$ | $p_c = p = 0.7$ | $p_c = p = 0.75$ | $p_c = p = 0.8$ | $p_c = p = 0.9$ |
|---|---|---|---|---|---|---|
| Without continuity | 0.794 | 0.825 | 0.867 | 0.906 | 0.947 | 0.999 |

Two-stage[2], four-dose design

| | $p_c = p_1 = 0.5$ $p_{2,3,4} = 0.5$ | $p_c = p_1 = 0.6$ $p_{2,3,4} = 0.5$ | $p_c = p_1 = 0.7$ $p_{2,3,4} = 0.5$ | $p_c = p_1 = 0.75$ $P_{2,3,4} = 0.5$ | $p_c = p_1 = 0.8$ $P_{2,3,4} = 0.5$ | $p_c = p_1 = 0.9$ $p_{2,3,4} = 0.5$ |
|---|---|---|---|---|---|---|
| Max Resp. | 0.892 | 0.642 | 0.807 | 0.888 | 0.936 | 0.996 |
| SOC($\gamma$ = 0) | 0.847 | 0.582 | 0.780 | 0.869 | 0.927 | 0.996 |
| SOC($\gamma$ = 1) | 0.841 | 0.563 | 0.759 | 0.853 | 0.916 | 0.995 |
| SOC($\gamma$ = 2) | 0.833 | 0.545 | 0.734 | 0.835 | 0.904 | 0.994 |
| SOC($\gamma$ = 3) | 0.830 | 0.536 | 0.700 | 0.791 | 0.866 | 0.992 |
| Bonfferro. | 0.755 | 0.487 | 0.668 | 0.765 | 0.838 | 0.983 |

[1]Results in the table are based on 10000 simulations of 175 subjects in each group.
[2]Two-stage means dose selection takes place at the first quarter of total sample.

Max Response: $\hat{p}_u - \hat{p}_c \pm 1.96 \sqrt{\hat{\sigma}_u^2 + \hat{\sigma}_c^2}$, SOC: $\hat{p}_t - \hat{p}_c \pm 1.96 \sqrt{\alpha^2 \hat{\sigma}_T^2 + (1-\alpha)^2 \hat{\sigma}_{eff}^2 + \hat{\sigma}_c^2}$, Bonfferroni Adjustment: $\hat{p}_u - \hat{p}_c \pm 2.50 \sqrt{\hat{\sigma}_u^2 + \hat{\sigma}_c^2}$.

Same procedure as in Case 1 could be employed to design a three-dose trial for appropriate sample size and allocation.

Case 4

Said method can also be applied to multiple dose clinical trials in which the drug effect is measured by a continuous variable, such as reduction in blood pressure, or in HIV viral loads. Suppose that we want to select a dose which makes the maximum reduction in blood pressure or in HIV viral load. Let $\bar{x}_s$ be the maximum of average observed reductions of each dose group. That is, $\bar{x}_s$=max $\{\bar{x}_i, i=1,2, \ldots, m\}$ assuming that there are m dose groups and each group's observed average blood pressure reduction is $\bar{x}_i$. Let $x_s$ be the true reduction in blood pressure or in HIV viral load of the selected dose group out of the true reduction $x_i$ of each dose group. Then $x_s = x_i$ if $\bar{x}_s = \bar{x}_i$. The true reduction, $x_s$, is likely overestimated by observed average reduction $\bar{x}_s$. The probability density function of the difference, $\bar{x}_s - x_s$, is given in Appendix A if we replace $p_i$ by $x_i$ and $\sigma_i^2$ by $\sigma_i^2/\alpha N$. This is because the sample average $\bar{x}_i$ is asymptotically normally distributed $N(x_i, \sigma_i^2/\alpha N)$. We assume that the selected dose of the test drug is to compare with a standard treatment. Let $\bar{y}$ be the average reduction of blood pressure in the standard treatment group. We will use confidence interval for the difference of reduction in blood pressure between the selected dose of the test drug and the standard treatment to make an inference of equivalence or superiority of the test drug.

Depending on how many doses to test, data analyzing steps follow the same procedure in case 1, 2 or 3. But an extra step is needed to ensure that variances of the interested variable in different doses do not differ too much. Numerical comparison shows that the true probability density function of the difference, $\bar{x}_s - x_s$, will not be nicely approximated by a normal density function when ratio of variances of two doses exceeds a range of [⅓, 3]. For this reason, we will estimate the range of ratio of variances among the doses to determine whether the method could be appropriately used for estimation and comparison. The procedure of data analyzing comprises following steps:

(a) Determining N, the number of total patients in the selected dose group at the end of trial, and $\alpha$ between 0 and 1, a proportion of N patients in each dose group enrolled by the time of dose selection. N and $\alpha$ are determined by the claims of the test drug intended to prove in the clinical trial, the power of statistical tests and feasibility to run such a trial within a reasonable budget and time frame. Some established methods in reference [3] and [4] can be used to determine the initial values of N and $\alpha$.

(b) Selecting a dose of the test drug by the time when $\alpha N$ patients in each dose group finish their treatment and are ready for evaluation. Let $\bar{x}_i$ be the reduction of blood pressure or viral load, etc., in the ith dose group. A dose will be selected if it has the maximum reduction in observation. That is, $x_s = x_i$ if $\bar{x}_s = \bar{s}_i$. $x_s$ is the true reduction of the selected dose and $\bar{x}_s = \max\{\bar{x}_i, i=1,2,\ldots,m\}$ is its estimate.

(c) Estimating variances of each dose group by $$\hat{\sigma}_i^2 = \left(\sum (x_{ik} - \bar{x}_i)\right)^2 / \alpha N$$

and constructing a $(1-\beta)\%$ confidence interval of the ratio of the maximum variance to the minimum variance of the dose groups. $\beta$ is normally chosen as 0.05, or 0.10. Let $F_\eta^{-1}(d_1, d_2)$ be the reciprocal of $\eta$th quantile of F-distribution with degree of freedom $d_1$, $d_2$. Then, the confidence interval of the ratio is (lower bound, upper bound)

$$\frac{\text{Lower}}{\text{bound}} = \frac{\max\{\hat{\sigma}_i^2, i=1,2,\ldots,m\}}{\min\{\hat{\sigma}_i^2, i=1,2,\ldots,m\}} F_{1-\beta/2}^{-1}(\alpha N - 1, \alpha N - 1) \quad (15)$$

$$\frac{\text{Upper}}{\text{bound}} = \frac{\max\{\hat{\sigma}_i^2, i=1,2,\ldots,m\}}{\min\{\hat{\sigma}_i^2, i=1,2,\ldots,m\}} F_{\beta/2}^{-1}(\alpha N - 1, \alpha N - 1) \quad (16)$$

If this confidence interval is within [⅓, 3], then go to next step. Otherwise stop here, it may not be appropriate to use this method.

(d) Estimating the bias of the difference of the estimated reduction and true reduction $\bar{x}_s - x_s$ by $\hat{b}_{SOC}(\gamma)$. $\hat{b}_{SOC}(\gamma)$ is in formula of step (c) of Case 1, 2 or 3 according to the number of doses in the trial, $\hat{p}_i$ and $\hat{\sigma}_i^2$ in the formula should be replaced by $\bar{x}_i$ and $\hat{\sigma}_i^2/\alpha N$ respectively. That is, if there are only two dose groups of the test drug, then $\hat{b}_{SOC}(\gamma) = \hat{b}_{12}(\gamma)$, where $$\hat{b}_{12}(\gamma) = \sqrt{(\hat{\sigma}_1^2 + \hat{\sigma}_2^2)/(2\pi\alpha N)} \, e^{-((i-1)\gamma)^2/2}, \text{ when} \quad (17)$$

$$(\bar{x}_1, \bar{x}_2, \hat{\sigma}_1^2, \hat{\sigma}_2^2) \in A_i, i=1, 2, \ldots$$

$$A_i = \left\{ (\bar{x}_1, \bar{x}_2, \hat{\sigma}_1^2, \hat{\sigma}_2^2) \mid (i-1)\gamma \le |\bar{x}_1 - \bar{x}_2|/\sqrt{(\hat{\sigma}_1^2 + \hat{\sigma}_2^2)/\alpha N} < i\gamma \right\}. \quad (18)$$

If there are three dose groups of the test drug, then $\hat{b}_{SOC}(\gamma) = \hat{b}_{12}\Phi(0,$ $\bar{x}_3 - \bar{x}_{12}, (\hat{\sigma}_3^2 +$ $\hat{\sigma}_{12}^2)/\alpha N) + \hat{b}_{23}\Phi(0,$ $\bar{x}_1 - \bar{x}_{23}, (\hat{\sigma}_1^2 + \hat{\sigma}_{23}^2)/\alpha N) +$ $+ \hat{b}_{31}\Phi(0, \bar{x}_2 -$ $\bar{x}_{31}, (\hat{\sigma}_2^2 + \hat{\sigma}_{31}^2)/\alpha N) \quad (19)$ where $\bar{x}_{ij} = (\hat{\sigma}_i^2 \bar{x}_j + \hat{\sigma}_j^2 \bar{x}_i)/(\hat{\sigma}_i^2 + \hat{\sigma}_j^2)$, $\hat{\sigma}_{ij}^2 = \hat{\sigma}_i^2 \hat{\sigma}_j^2/(\hat{\sigma}_i^2 + \hat{\sigma}_j^2)$ and $\hat{b}_{ij}$ is in the formula of (17)

If there are four dose groups of the test drug, then $$\hat{b}_{SOC}(\gamma) = \sum_{i \ne j \ne k \ne l} \hat{b}_{ij} \hat{P}(i, j, k, l) \quad (20)$$

$\hat{b}_{ij}$ is in the formula of (17), $$\hat{P}(i, j, k, l) = \int_{-\infty}^{\infty} \varphi(u, \bar{x}_{ij}, \hat{\sigma}_{ij}^2/\alpha N) \Phi(u, \bar{x}_k, \hat{\sigma}_k^2/\alpha N) \Phi(u, \bar{x}_l, \hat{\sigma}_l^2/\alpha N) du.$$

(e) Estimating the variance of $\bar{x}_s - x_s$, by $\hat{\sigma}_T^2$, with the respective formula in step (d) of Case 1, 2, or 3 and also replacing $\hat{p}_i$ by $\bar{x}_i$, replacing $\hat{\sigma}_i^2$ by $\hat{\sigma}_i^2/\alpha N$ in the formula. That is, if there are only two dose groups of the test drug, $$\hat{\sigma}_T^2 = (\hat{\sigma}_1^2/\alpha N)\Phi(0, \bar{x}_2 - \bar{x}_1, (\hat{\sigma}_1^2 + \hat{\sigma}_2^2)/\alpha N) + \quad (21)$$

$$(\hat{\sigma}_2^2/\alpha N)\Phi(0, \bar{x}_1 - \bar{x}_2, (\hat{\sigma}_1^2 + \hat{\sigma}_2^2)/\alpha N) +$$

$$\frac{(\bar{x}_1 - \bar{x}_2)(\hat{\sigma}_2^2 - \hat{\sigma}_1^2)/\alpha N}{\sqrt{2\pi(\hat{\sigma}_1^2 + \hat{\sigma}_2^2)/\alpha N}} e^{-\frac{(\bar{x}_1 - \bar{x}_2)^2}{2(\hat{\sigma}_1^2 + \hat{\sigma}_2^2)/\alpha N}} -$$

$$\frac{(\hat{\sigma}_2^2 + \hat{\sigma}_1^2)}{2\pi\alpha N} e^{-\frac{(\bar{x}_1 - \bar{x}_2)^2}{(\hat{\sigma}_1^2 + \hat{\sigma}_2^2)/\alpha N}}$$

If there are three dose groups of the test drug, $$\hat{\sigma}_T^2 = \int_{-\infty}^{+\infty} t^2 \hat{f}(t) dt - \left(\int_{-\infty}^{+\infty} t \hat{f}(t) dt\right)^2 \quad (22)$$

where $$\hat{f}(t) = \sum_{i=1}^{3} \varphi(t + \bar{x}_i, \bar{x}_i, \hat{\sigma}_i^2/\alpha N) \prod_{j \neq i} \Phi(t + \bar{x}_i, \bar{x}_j, \hat{\sigma}_j^2/\alpha N).$$

If there are four dose groups of the test drug, $$\hat{\sigma}_T^2 = \int_{-\infty}^{+\infty} t^2 \hat{f}(t) dt - \left(\int_{-\infty}^{+\infty} t \hat{f}(t) dt\right)^2, \quad (23)$$

where $$\hat{f}(t) = \sum_{i=1}^{4} \varphi(t + \bar{x}_i, \bar{x}_i, \hat{\sigma}_i^2/\alpha N) \prod_{j \neq i} \Phi(t + \bar{x}_i, \bar{x}_j, \hat{\sigma}_j^2/\alpha N).$$

(f) Enrolling $(1-\alpha)N$ patients per group in the selected dose group and the control group if $\alpha$ 1, estimating the reduction of the selected dose group by $\bar{x}_{aft}$, sample average of reduction from the dose selection to the end of clinical trial, and estimating the variance of $\bar{x}_{aft}$ by $\hat{\sigma}_{aft}^2$, $$\hat{\sigma}_{aft}^2 = \sum_{k=1}^{(1-\alpha)N} (x_{sk} - \bar{x}_{aft})^2 / ((1-\alpha)N)^2 \quad (24)$$

are samples of the selected dose group after dose selection. If $\alpha=1$, go to step (g).

(g) Estimating the true reduction of the control group by $\bar{y}$, the sample mean of reduction in blood pressure in the control group, and estimating the variance of $\bar{y}$ in the control group by $\hat{\sigma}_c^2$, $$\hat{\sigma}_c^2 = \sum_{k=1}^{N} (y_k - \bar{y})^2 / N^2 \quad (25)$$

sum up from total sample in the control group.

(h) Constructing an estimate for the true reduction of the selected dose by $$\hat{x}_t = \alpha \bar{x}_s + (1-\alpha)\bar{x}_{aft} - \alpha \hat{b}_{SOC}(\gamma) \quad (26),$$

and an estimate for the variance of $\hat{x}$, by $\alpha^2 \hat{\sigma}_T^2 + (1-\alpha)^2 \hat{\sigma}_{aft}^2$.

(i) Constructing a two-sided 95% confidence interval for the difference of cure rates between the selected dose of the test drug and the standard treatment $$95\% \ C.I. = \hat{x}_t - \bar{y} \pm 1.96\sqrt{\alpha^2 \hat{\sigma}_T^2 + (1-\alpha)^2 \hat{\sigma}_{aft}^2 + \hat{\sigma}_c^2} \quad (27)$$

(j) Performing a statistical test as to show that the test drug is better than the standard treatment, and surrendering the significance of difference called p value, $$p = 1 - \Phi(\hat{d}, 0, 1) + \Phi(-\hat{d}, 0, 1), \text{ and} \quad (28)$$

$$\hat{d} = (\hat{x}_t - \bar{y}) / \sqrt{\alpha^2 \hat{\sigma}_T^2 + (1-\alpha)^2 \hat{\sigma}_{aft}^2 + \hat{\sigma}_c^2}.$$

Application of above data analyzing procedure is the same as in Case 1.

Validation of method

As has been pointed out earlier, probability density function of $\bar{x}_s - x_s$ may not be approximated by a density function of normal distribution when ratio of variances of dose groups is beyond the range of [1/3, 3]. Therefore, an extra step is added to check whether this method is applicable. Properties of this method will be demonstrated by an example using Monte Carlo approach. Assume that we want to prove that a test drug can reduce viral load more significantly than the standard treatment. We want to make sure that chance for a method to claim superiority of the test drug is no more than 0.025 when true effect of the test drug and the standard treatment are the same. There are two doses of the test drug to be tested. Sixty-four patients in each group are going to be recruited by the end of clinical trial. One of the two doses will be selected when the first half of 64 patients in each dose group completes the trial. Based on previous experience of the standard treatment, viral load can be reduced 100 units after the treatment, and the standard deviation is about 25 units. Therefore, the ideal method should be such that it has less than 0.025 of chance to claim superiority when none of two doses surpasses the standard treatment in reduction of viral load, meanwhile its chance to claim superiority is as high as possible when at least a dose of test drug is better than the standard treatment. For simplicity, we assume the standard deviation of test drug is also 25 units. Table 10 shows that Max Response claims superiority of the test drug in a probability of 4.2% even when both two doses of the test drug have the same average reduction of 100 units of viral load. SOC(2) has a chance of 2.58% and chance for SOC(3) is 2.41%. Bonfferroni Adjustment has the lowest chance of 1.52%. However, chances for Bonfferroni Adjustment to claim superiority are affected when a dose of test drug reduces more viral load. If both doses of the test drug lower viral load 106 units, chances for Bonfferroni Adjustment to claim superiority of 21.7%, while chances for SOC(2) and SOC(3) are 28.5% and 28.1%. If only one dose of the test drug reduces viral load 112 units, power of Bonfferroni Adjustment is 62.2% compared to 71.1% and 68.7% for SOC(2) and SOC(3), respectively. When both doses of the test drug reduce viral load 12 units more than the standard treatment, Bonfferroni Adjustment still has lower probability (73.7%) to claim superiority than SOC(2) and SOC(3), which are 80.0% and 79.8%. Therefore, SOC is better than Max Response and Bonfferroni Adjustment in handling various situations.

TABLE 10

| | Probability of claiming superiority[1] | | | |
|---|---|---|---|---|
| Reduction in control group | $x_c = 100$ | $x_c = 100$ | $x_c = 100$ | $x_c = 100$ |
| Reduction in Test drug groups | $x_1 = 100$, $x_2 = 100$ | $x_1 = 106$, $x_2 = 106$ | $x_1 = 112$, $x_2 = 100$ | $x_1 = 112$, $x_2 = 112$ |
| Max Response | 0.0416 | 0.371 | 0.765 | 0.857 |
| SOC($\gamma = 0$) | 0.0318 | 0.313 | 0.740 | 0.817 |
| SOC($\gamma = 1$) | 0.0289 | 0.297 | 0.726 | 0.806 |
| SOC($\gamma = 2$) | 0.0258 | 0.285 | 0.711 | 0.800 |
| SOC($\gamma = 3$) | 0.0241 | 0.281 | 0.687 | 0.798 |

TABLE 10-continued

Probability of claiming superiority[1]

| Reduction in control group | $x_c = 100$ | $x_c = 100$ | $x_c = 100$ | $x_c = 100$ |
|---|---|---|---|---|
| Bonfferroni Adjustment | 0.0152 | 0.217 | 0.622 | 0.737 |

[1]Results based on 20000 simulations of 64 patients per group and dose selection takes place at the first half of 64 patients of each dose group. Assume standard deviation of each group is 25.

Same procedure as in Case 1 could be employed to design a multiple dose clinical trial measured by a continuous variable for appropriate sample size and allocation So far, detailed description of the method in each case has been presented. Some formulas used in the method are deduced in appendices.

APPENDIX A

We are going to prove the density function of $\hat{p}_s - p_{\tilde{s}}$ in two-dose trial is $$\varphi(t + p_1, p_1, \sigma_1^2)\Phi(t + p_1, p_2, \sigma_2^2) + \varphi(t + p_2, p_2, \sigma_2^2)\Phi(t + p_2, p_1, \sigma_1^2).$$

Let the true response rates of Dose 1, Dose 2 be $p_1, p_2$, and $\hat{p}_s = \max(\hat{p}_1, \hat{p}_2)$. $\hat{p}_1 \sim N(p_1, \sigma_1^2)$ and $\hat{p}_2 \sim N(p_2, \sigma_2^2)$.

$$p_{\tilde{s}} = \begin{cases} p_1, & \text{if } \hat{p}_1 \geq \hat{p}_2; \\ p_2, & \text{if } \hat{p}_2 > \hat{p}_1. \end{cases}$$

Then, the density function of $\hat{p}_s - p_{\tilde{s}}$ is $$P(\hat{p}_s - p_{\tilde{s}} < t) = P(\hat{p}_s - p_{\tilde{s}} < t, \hat{p}_s = \hat{p}_1) + P(\hat{p}_s - p_{\tilde{s}} < t, \hat{p}_s = \hat{p}_2)$$

$$= P(\hat{p}_1 < t + p_1, \hat{p}_2 < t + p_1, \hat{p}_1 \geq \hat{p}_2) + P(\hat{p}_1 < t + p_2, \hat{p}_2 < t + p_2, \hat{p}_2 > \hat{p}_1)$$

$$= \int_{-\infty}^{t+p_1} \varphi(x, p_1, \sigma_1^2) \int_{-\infty}^{x} \varphi(y, p_2, \sigma_2^2) dy\, dx + \int_{-\infty}^{t+p_2} \varphi(y, p_2, \sigma_2^2) \int_{-\infty}^{y} \varphi(x, p_1, \sigma_1^2) dx\, dy$$

Thus, the density function of $\hat{p}_s - p_{\tilde{s}}$ is $$\frac{dP(\hat{p}_s - p_{\tilde{s}} < t)}{dt} = \varphi(t + p_1, p_1, \sigma_1^2)\int_{-\infty}^{t+p_1} \varphi(y, p_2 \sigma_2^2) dy + \varphi(t + p_2, p_2, \sigma_2^2)\int_{-\infty}^{t+p_2} \varphi(x, p_1, \sigma_1^2) dx$$

$$= \varphi(t + p_1, p_1, \sigma_1^2)\Phi(t + p_1, p_2, \sigma_2^2) + \varphi(t + p_2, p_2, \sigma_2^2)\Phi(t + p_2, p_1, \sigma_1^2)$$

More generally, probability density function of $\hat{p}_s - p_{\tilde{s}}$ for multiple doses is $$f(t) = \sum_{i=1}^{K} \varphi(t + p_i, p_i, \sigma_i^2) \prod_{j \neq i} \Phi(t + p_i, p_j, \sigma_j^2)$$

APPENDIX B

The mean and variance of $\hat{p}_s - p_{\tilde{s}}$ in a two-dose design can be calculated from the above density function. Calculation is simple but tedious. Only critical steps in the calculation will be presented here.

$$E(\hat{p}_s - p_{\tilde{s}}) = \int_{-\infty}^{\infty} t\varphi(t + p_1, p_1, \sigma_1^2)\Phi(t + p_1, p_2, \sigma_2^2) dt + \int_{-\infty}^{\infty} t\varphi(t + p_2, p_2, \sigma_2^2)\Phi(t + p_2, p_2, \sigma_1^2) dt$$

The first integral of the sum could be further expressed as follows:

$$\int_{-\infty}^{\infty} t\varphi(t + p_1, p_1, \sigma_1^2)\Phi(t + p_1, p_2, \sigma_2^2) dt = \int_{-\infty}^{\infty} t\varphi(t + p_1, p_1, \sigma_1^2) \int_{-\infty}^{t+p_1} \varphi(u, p_2, \sigma_2^2) du\, dt$$

$$= \int_{-\infty}^{\infty} \varphi(u, p_2, \sigma_2^2) \int_{u-p_1}^{\infty} t\varphi(t + p_1, p_1, \sigma_1^2) dt\, du$$

APPENDIX B-continued $$= \int_{-\infty}^{\infty} \varphi(u, p_2, \sigma_2^2)\sigma_1^2 \varphi(u, p_1, \sigma_1^2) du$$

$$= \frac{\sigma_1^2}{\sqrt{2\pi(\sigma_1^2 + \sigma_2^2)}} e^{-\frac{(p_1-p_2)^2}{2(\sigma_1^2+\sigma_2^2)}}$$

Similarly, the second integral also has a simple expression and sum of the two parts is the mean of $\hat{p}_s - p_{\hat{s}}$ as we expected.

The variance of $\hat{p}_s - p_{\hat{s}}$ can be obtained by $E(\hat{p}_s - p_{\hat{s}})^2 - (E(\hat{p}_s - p_{\hat{s}}))^2$. As the way to calculate the mean, the second moment of $\hat{p}_s - p_{\hat{s}}$ is the sum of the two integrals. Here is the first half.

$$\int_{-\infty}^{\infty} t^2 \varphi(t+p_1, p_1, \sigma_1^2)\Phi(t+p_1, p_2, \sigma_2^2) dt = \int_{-\infty}^{\infty} t^2 \varphi(t+p_1, p_1, \sigma_1^2) \int_{-\infty}^{t+p_1} \varphi(u, p_2, \sigma_2^2) du\, dt$$

$$= \int_{-\infty}^{\infty} \varphi(u, p_2, \sigma_2^2) \int_{t-p_1}^{\infty} t^2 \varphi(t+p_1, p_1, \sigma_1^2) dt\, du$$

$$= \int_{-\infty}^{\infty} \varphi(u, p_2, \sigma_2^2)\sigma_1^2(u-p_1)\varphi(u, p_1, \sigma_1^2) du + \int_{-\infty}^{\infty} \varphi(u, p_2, \sigma_2^2) \int_{t-p_1}^{\infty} \sigma_1^2 \varphi(t+p_1, p_1, \sigma_1^2) dt\, du$$

The first term at the right side of the last equation could be simplified. Let $p_{12} = (\sigma_1^2 p_2 + \sigma_2^2 p_1)/(\sigma_1^2 + \sigma_2^2)$ and $\sigma_{12}^2 = \sigma_1^2 \sigma_2^2/(\sigma_1^2 + \sigma_2^2)$. Then, $$\int_{-\infty}^{\infty} \varphi(u, p_2, \sigma_2^2)\sigma_1^2(u-p_1)\varphi(u, p_1, \sigma_1^2) du$$

$$= \int_{-\infty}^{\infty} \sigma_1^2(u-p_1)\varphi(u, p_{12}, \sigma_{12}^2)\sigma_{12}\left(\sqrt{2\pi}\,\sigma_1\sigma_2\right)^{-1} e^{-\frac{(p_1-p_2)^2}{2(\sigma_1^2+\sigma_2^2)}} du$$

$$= (p_{12} - p_1)\sigma_1^2\left(\sigma_{12}\left(\sqrt{2\pi}\,\sigma_1\sigma_2\right)\right)^{-1} e^{-\frac{(p_1-p_2)^2}{2(\sigma_1^2+\sigma_2^2)}} = (p_2 - p_1)\left(\sigma_1^4\left(\sqrt{2(\pi(\sigma_1^2+\sigma_2^2))^3}\right)\right)^{-1} e^{-\frac{(p_1-p_2)^2}{2(\sigma_1^2+\sigma_2^2)}}$$

The second term is simplified by a transformation, $x = (u + t - p_1)/2$, $y = (u - t - p_1)/2$ $$\int_{-\infty}^{\infty} \varphi(u, p_2, \sigma_2^2) \int_{t-p_1}^{\infty} \sigma_1^2 \varphi(t+p_1, p_1, \sigma_1^2) dt\, du$$

$$= \int_{-\infty}^{\infty} dx \int_{-\infty}^{0} \varphi(x+y+p_1, p_2, \sigma_2^2)\sigma_1^2 \varphi(x-y+p_1, p_1, \sigma_1^2)|J(u, t \to x, y)| dy$$

$$= \int_{-\infty}^{0} dy \int_{-\infty}^{\infty} \varphi(x, p_2 - y - p_1, \sigma_2^2)\sigma_1^2 \varphi(x, y, \sigma_1^2) 2 dx$$

$$= \int_{-\infty}^{0} \frac{2\sigma_1^2}{\sqrt{2\pi}\,\sigma_1\sigma_2} \frac{\sigma_1\sigma_2}{\sqrt{\sigma_1^2+\sigma_2^2}} e^{-\frac{(p_2-y-p_1-y)^2}{2(\sigma_1^2+\sigma_2^2)}} dy = \sigma_1^2 \Phi(0, p_2 - p_1, \sigma_1^2 + \sigma_2^2).$$

The other half of $E(\hat{p}_s - p_{\hat{s}})^2$ can be obtained similarly. The final formula of $E(\hat{p}_s - p_{\hat{s}})^2$ after combining all these results is of a closed form as shown below, $$\sigma_1^2 \Phi(0, p_2 - p_1, \sigma_1^2 + \sigma_2^2) + \sigma_2^2 \Phi(0, p_1 - p_2, \sigma_1^2 + \sigma_2^2) + \frac{(p_1 - p_2)(\sigma_2^2 - \sigma_1^2)}{\sqrt{2\pi(\sigma_1^2+\sigma_2^2)}} e^{-\frac{(p_1-p_2)^2}{2(\sigma_1^2+\sigma_2^2)}}.$$

APPENDIX C

We will show the formula of $E(\hat{p}_s - p_{\hat{s}})$ for the cases in which there are multiple doses of test drug for selection. In practical situations, three, or four doses are very likely in dose finding investigation. The mean of $\hat{p}_s - p_{\hat{s}}$ in multiple dose designs is the sum of the weighted means of every two doses. Let $b_{ij}$, $p_{ij}$, $\sigma_{ij}^2$ be the bias, combined mean and variance of two dose design given in Appendix B. Then, the bias of a three dose trial is $b_{12}\Phi(0, p_3 - p_{12}, \sigma_3^2 + \sigma_{12}^2) + b_{23}\Phi(0, p_1 - p_{23}, \sigma_1^2 + \sigma_{23}^2) + b_{31}\Phi(0, p_2 - p_{31}, \sigma_2^2 + \sigma_{31}^2)$ Remember that propability density function of $\hat{p}_s - p_{\hat{s}}$ of three doses given in Appendix A has three terms and we finally calculate the integral of the first term.

APPENDIX C-continued $$\int_{-\infty}^{\infty} t\varphi(t+p_1, p_1, \sigma_1^2)\Phi(t+p_1, p_2, \sigma_2^2)\Phi(t+p_1, p_3, \sigma_3^2)dt$$

$$= \int_{-\infty}^{\infty} t\varphi(t+p_1, p_1, \sigma_1^2) \int_{-\infty}^{t+p_1} \varphi(u, p_2, \sigma_2^2) \int_{-\infty}^{t+p_1} \varphi(w, p_3, \sigma_3^2) dw \, du \, dt$$

$$= \int_{-\infty}^{\infty} \varphi(u, p_2, \sigma_2^2) du \int_{-\infty}^{\infty} \varphi(w, p_3, \sigma_3^2) dw \int_{\max(u-p_1, w-p_1)}^{\infty} t\varphi(t+p_1, p_1, \sigma_1^2) dt$$

$$= \int_{-\infty}^{\infty} \int_{-\infty}^{\infty} \varphi(u, p_2, \sigma_2^2)\varphi(w, p_3, \sigma_3^2)\sigma_1^2 \varphi(\max(u-p_1, w-p_1), 0, \sigma_1^2) du \, dw$$

$$= \int_{-\infty}^{\infty} \int_{-\infty}^{u} \varphi(u, p_2, \sigma_2^2)\varphi(w, p_3, \sigma_3^2)\sigma_1^2 \varphi(u-p_1, 0, \sigma_1^2) du \, dw + \int_{-\infty}^{\infty} \int_{-\infty}^{w} \varphi(u, p_2, \sigma_2^2)\varphi(w, p_3, \sigma_3^2)\sigma_1^2 \varphi(w-p_1, 0, \sigma_1^2) du \, dw$$

$$= \int_{-\infty}^{\infty} \int_{-\infty}^{u} \varphi(u, p_{12}, \sigma_{12}^2)\varphi(w, p_3, \sigma_3^2) \frac{\sigma_1^2}{\sqrt{2\pi(\sigma_1^2 + \sigma_2^2)}} e^{-\frac{(p_1-p_2)^2}{2(\sigma_1^2+\sigma_2^2)}} du \, dw + \int_{-\infty}^{\infty} \int_{-\infty}^{w} \varphi(u, p_2, \sigma_2^2)\varphi(w, p_{13}, \sigma_{13}^2) \frac{\sigma_1^2}{\sqrt{2\pi(\sigma_1^2 + \sigma_3^2)}} e^{-\frac{(p_1-p_3)^2}{2(\sigma_1^2+\sigma_3^2)}} du \, dw$$

$$= \frac{\sigma_1^2}{\sqrt{2\pi(\sigma_1^2 + \sigma_2^2)}} e^{-\frac{(p_1-p_2)^2}{2(\sigma_1^2+\sigma_2^2)}} \Phi(0, p_3 - p_{12}, \sigma_3^2 + \sigma_{12}^2) + \frac{\sigma_1^2}{\sqrt{2\pi(\sigma_1^2 + \sigma_3^2)}} e^{-\frac{(p_1-p_3)^2}{2(\sigma_1^2+\sigma_3^2)}} \Phi(0, p_2 - p_{13}, \sigma_2^2 + \sigma_{13}^2)$$

The last equation is held if we use the same variable transformation as in Appendix B.
Similar calculations apply to other two terms of the probability density function and the sum of all these terms is of the form we expected.
The mean of $\hat{p}_s - p_{\tilde{s}}$ for a four dose design is $$\sum_{i \neq j \neq k \neq l} b_{ij} P(i, j, k, l),$$

in which $b_{ij}$ is the mean of $\hat{p}_s - p_{\tilde{s}}$ of a two-dose design as Appendix A, and $P(i, j, k, l)$ is the brobability defined by $$\int_{-\infty}^{\infty} \varphi(u, p_{ij}, \sigma_{ij}^2) \Phi(u, p_k \sigma_k^2) \Phi(u, p_l, \sigma_l^2) du.$$

Reference
1. Sankoh, A. J., Huque, M. F. and Dubey, S. D. 'Some comments on frequently used multiple endpoint adjustment methods in clinical trials', Statistics in Medicine, 16, 2529–2542 (1997).
2. D'Agostino, R. B., Massaro, J., Hwan, H. and Cabral, H. 'Strategies for dealing with multiple comparisons in confirmatory clinical trials', Drug Information Journal, 27, 625–641 (1993).
3. Lachin, J. M., 'Introduction to sample size determination and power analysis for clinical trials', Controlled Clinical Trials, 2, 93–113 (1981).
4. Makuch, R. and Simon, R., 'Sample size requirements for evaluating a conservative therapy', Cancer Treatment, 62, 1037–1040 (1978).

I claim:
1. A method for evaluating drug effect in the a multiple dose clinical trial comprising:
   (a) Selecting N, the number of patients at the selected dose group by the end of trial, and α between 0 aid 1, a proportion of N patients per group enrolled by the time of dose selection,
   (b) Estimating drug effect of each dose group using the proportion of success among αN patients in each dose group when they finish their treatment evaluation,
   (c) Selecting a dose of the test drug which has the highest observed success rate,
   (d) Estimating the bias between the estimated drug effect and the true drug effect of the selected dose group as

$$\hat{b}_{12}(\gamma) = \sqrt{(\hat{\sigma}_1^2 + \hat{\sigma}_2^2)/(2\pi)} \, e^{-((i-1)\gamma)^2/2}, \quad (1)$$

when $(\hat{p}_1, \hat{p}_2, \hat{\sigma}_1^2, \hat{\sigma}_2^2) \in A_i, i = 1, 2, \cdots$ where $A_i =$ $$\left\{ (\hat{p}_1, \hat{p}_2, \hat{\sigma}_1^2, \hat{\sigma}_2^2) \mid (i-1)\gamma \leq \left| \hat{p}_1 - \hat{p}_2 \right| / \sqrt{\hat{\sigma}_1^2 + \hat{\sigma}_2^2} < i\gamma \right\},$$

if two doses of the test drug are tested; as $$\hat{b}_{SOC}(\gamma) = \hat{b}_{12} \Phi(0, \hat{p}_3 - \hat{p}_{12}, \hat{\sigma}_3^2 + \hat{\sigma}_{12}^2) + \qquad (9)$$

$$\hat{b}_{23} \Phi(0, \hat{p}_1 - \hat{p}_{23}, \hat{\sigma}_1^2 + \hat{\sigma}_{23}^2) + \hat{b}_{31} \Phi(0, \hat{p}_2 - \hat{p}_{31}, \hat{\sigma}_2^2 + \hat{\sigma}_{31}^2)$$

if three doses of the test drug are tested; or as $$\hat{b}_{SOC}(\gamma) = \sum_{i \neq j \neq k \neq l} \hat{b}_{ij} \hat{P}(i, j, k, l) \qquad (11)$$

where $$\hat{P}(i, j, k, l) = \int_{-\infty}^{+\infty} \varphi(u, \hat{p}_{ij}, \hat{\sigma}_{ij}^2) \Phi(u, \hat{p}_k \hat{\sigma}_k^2) \Phi(u, \hat{p}_l, \hat{\sigma}_l^2) du,$$

if four doses of the test drug are tested,
   (e) Estimating the variance of $\hat{p}_s - p_{\tilde{s}}$, the difference between the estimated drug effect and the true drug effect of the selected dose group as $$\hat{\sigma}_T^2 = \hat{\sigma}_1^2 \Phi(0, \hat{p}_2 - \hat{p}_1, \hat{\sigma}_1^2 + \hat{\sigma}_2^2) + \hat{\sigma}_2^2 \Phi(0, \hat{p}_1 - \hat{p}_2, \hat{\sigma}_1^2 + \hat{\sigma}_2^2) +$$

$$\frac{(\hat{p}_1 - \hat{p}_2)(\hat{\sigma}_2^2 - \hat{\sigma}_1^2)}{\sqrt{2\pi(\hat{\sigma}_1^2 + \hat{\sigma}_2^2)}} e^{-\frac{(\hat{p}_1 - \hat{p}_2)^2}{2(\hat{\sigma}_1^2 + \hat{\sigma}_2^2)}} - \frac{(\hat{\sigma}_2^2 + \hat{\sigma}_1^2)}{2\pi} e^{-\frac{(\hat{p}_1 - \hat{p}_2)^2}{(\hat{\sigma}_1^2 + \hat{\sigma}_2^2)}}$$

if two doses of the test drug are tested; as $$\hat{\sigma}_T^2 = \int_{-\infty}^{+\infty} t^2 \hat{f}(t) dt - \left( \int_{-\infty}^{+\infty} t \hat{f}(t) dt \right)^2$$

where $$\hat{f}(t) = \sum_{i=1}^{3} \varphi(t + \hat{p}_1, \hat{p}_1, \hat{\sigma}_1^2) \prod_{j \neq i} \Phi(t + \hat{p}_1, \hat{p}_j, \hat{\sigma}_j^2),$$

if three doses of the test drug are tested; or as $$\hat{\sigma}_Y^2 = \int_{-\infty}^{+\infty} t^2 \hat{f}(t) dt - \left( \int_{-\infty}^{+\infty} t \hat{f}(t) dt \right)^2$$

where $$\hat{f}(t) = \sum_{i=1}^{\alpha} \varphi(t + \hat{p}_1, \hat{p}_1, \hat{\sigma}_i^2) \prod_{j \neq i} \Phi(t + \hat{p}_1, \hat{p}_j, \hat{\sigma}_j^2),$$

if four doses of the test drug are tested, (f) If α 1, enrolling (1-α)N patients per group to the selected dose group and the control group; otherwise, go to step (h), (g) Estimating the drug effect of the selected dose group after dose selection using the proportion of success among the patients in the selected group enrolled after the dose selection and estimating the variance of this estimate as $$\hat{\sigma}_{aft}^2 \hat{p}_{aft}(1 \hat{p}_{aft})/1-\alpha)N \quad (3).$$

(h) Estimating the drug effect of the control group using the proportion of success in the total patients of the control group and estimating the variance of this estimate as $$\hat{\sigma}_c^2 = \hat{p}_c(1-\hat{p}_c)/N \quad (4),$$

(i) Constructing the overall estimate for the drug effect of the selected dose as $$\hat{p} = \alpha \hat{p}_s + (1-\alpha)\hat{p}_{aft} - \alpha \hat{b}_{12}(\gamma) \quad (5),$$

(j) Constructing a two-sided 95% confidence interval for the difference of drug effects between the selected dose of the test drug and the control treatment as $$95\% \ C.I. = \hat{p}_t - \hat{p}_c \pm 1.96 \sqrt{\alpha^2 \hat{\sigma}_T^2 + (1-\alpha)^2 \hat{\sigma}_{aft}^2 + \hat{\sigma}_c^2}, \quad (6)$$

(k) Calculating p value, the statistical significance of the difference for the drug effects between the selected dose of the test drug and the control treatment as $$p = 1 - \Phi(\hat{d}, 0, 1) + \Phi(-\hat{d}, 0, 1), \quad (7)$$

where $$\hat{d} = (\hat{p}_t - \hat{p}_c) / \sqrt{\alpha^2 \hat{\sigma}_T^2 + (1-\alpha)^2 \hat{\sigma}_{aft}^2 + \hat{\sigma}_c^2}, \quad (8)$$

(l) Using the significance level in step (k), the confidence interval in step (j), the overall estimate for the drug effect of the selected dose in step (i), estimate of bias in step (d) or the estimate of the variance of $\hat{p}_s - \hat{p}_{\hat{s}}$ in step (e) to justify the efficacy of the selected dose of the test drug in the New Drug Application of the test drug, (m) Using the significance level in step (k), the confidence interval in step (j), the overall estimate for the drug effect of the selected dose in step (i), estimate of bias in step (d) or the estimate of the variance $\hat{p}_s - \hat{p}_{\hat{s}}$ in step (e) to justify the efficacy of the selected dose of the test drug in the labeling of the test drug, (n) Using the significance level in step (k), the confidence interval in step (j), the overall estimate for the drug effect of the selected dose in step (i), estimate of bias in step (d) or the estimate of the variance $\hat{p}_s - \hat{p}_{\hat{s}}$ in step (e) to justify the efficacy of the selected dose of the test drug in the advertisement of the test drug.

2. The method of claim 1, wherein doses are different formulations, different strengths, different duration of treatment, or different combinations with other drug.

3. The method of claim 1, wherein drug effect is the rate of success of a treatment group in which patients are evaluated by success or failure, such as resolution of fever, free from infection, etc.

4. A method to simulate the probability of the method as described in claim 1 to accept a hypothesis about the drug effect of the test drug comprising:

(a) Presumptively assuming the true rate of success, $p_1$, for each treatment group, (b) Specifying the rules for the test drug to claim its equivalence or superior to the controlled treatment as such that, for the hypothesis of equivalence, the 95% confidence interval for the difference of the success rates, the test drug's minus the control's, must be no less than $-\Delta$ ($\Delta$ is usually chosen from a range of 0.25 to 0.05); for the hypothesis of superiority, the p value of the statistical test used must be less than $\epsilon$ ($\epsilon$ is usually chosen as 0.05), (c) Selecting a Repetition Number R (usually ranges from 5,000 to 1,000,000) as appropriate for the level of reliability for assessing the targeted probability, (d) Selecting N, the number of patients in each dose group to be enrolled to the trial, and α between 0 and 1, a proportion of N patients per group enrolled by the time of dose selection, (e) For each group in the clinical trial, generating by computer(s) from a binomial distribution, $b(N, 1, p_i)$, N random numbers of 0s for failures or 1s for successes, where $p_i$ is the assumed true rate of success for each treatment group in step (a), (f) Estimating drug effect in each dose group using the proportion of success in each dose group among the first αN patients in each dose group, (g) Selecting a dose of tie test drug which has the highest observed success rate, (h) Estimating the bias between the estimated drug effect and the true drug effect of the selected dose group as $$\hat{b}_{12}(\gamma) = \sqrt{(\hat{\sigma}_1^2 + \hat{\sigma}_2^2)/(2\pi)} \, e^{-((i-1)\gamma)^2/2}, \text{ when} \tag{1}$$

$$(\hat{p}_1, \hat{p}_2, \hat{\sigma}_1^2, \hat{\sigma}_2^2) \in A_i, i = 1, 2, \ldots$$

where $$A_i = \left\{ (\hat{p}_1, \hat{p}_2, \hat{\sigma}_1^2, \hat{\sigma}_2^2) \,\middle|\, (i-1)\gamma \le |\hat{p}_1 - \hat{p}_2|/\sqrt{\hat{\sigma}_1^2 + \hat{\sigma}_2^2} < i\gamma \right\}$$

if two doses of the test drug are tested; as $$\hat{b}_{SOC}(\gamma) = \hat{b}_{12}\Phi(0, \hat{p}_3 - \hat{p}_{12}, \hat{\sigma}_3^2 + \hat{\sigma}_{12}^2) + \tag{9}$$
$$\hat{b}_{23}\Phi(0, \hat{p}_1 - \hat{p}_{23}, \hat{\sigma}_1^2 + \hat{\sigma}_{23}^2) + \hat{b}_{31}\Phi(0, \hat{p}_2 - \hat{p}_{31}, \hat{\sigma}_2^2 + \hat{\sigma}_{31}^2)$$

if three doses of the test drug are tested, or as $$\hat{b}_{SOC}(\gamma) = \sum_{i \ne j \ne k \ne l} \hat{b}_{ij} \hat{P}(i, j, k, l) \tag{11}$$

where $$\hat{P}(i, j, k, l) = \int_{-\infty}^{\infty} \varphi(u, \hat{p}_{ij}, \hat{\sigma}_{ij}^2) \Phi(u, \hat{p}_k, \hat{\sigma}_k^2) \Phi(u, \hat{p}_l, \hat{\sigma}_l^2) du,$$

if four doses of the test drug are tested, (i) Estimating the variance of $\hat{p}_s - p_s$, the difference between the estimated drug effect and the true drug effect of the selected dose group as $$\hat{\sigma}_T^2 = \hat{\sigma}_1^2 \Phi(0, \hat{p}_2 - \hat{p}_1, \hat{\sigma}_1^2 + \hat{\sigma}_2^2) + \hat{\sigma}_2^2 \Phi(0, \hat{p}_1 - \hat{p}_2, \hat{\sigma}_1^2 + \hat{\sigma}_2^2) + \tag{2}$$
$$\frac{(\hat{p}_1 - \hat{p}_2)(\hat{\sigma}_2^2 - \hat{\sigma}_1^2)}{\sqrt{2\pi(\hat{\sigma}_1^2 + \hat{\sigma}_2^2)}} e^{-\frac{(\hat{p}_1-\hat{p}_2)^2}{2(\hat{\sigma}_1^2+\hat{\sigma}_2^2)}} - \frac{(\hat{\sigma}_2^2 + \hat{\sigma}_1^2)}{2\pi} e^{-\frac{(\hat{p}_1-\hat{p}_2)^2}{(\hat{\sigma}_1^2+\hat{\sigma}_2^2)}}$$

if two doses of the test drug are tested; as $$\hat{\sigma}_T^2 = \int_{-\infty}^{+\infty} t^2 \hat{f}(t)dt - \left( \int_{-\infty}^{+\infty} t\hat{f}(t)dt \right)^2 \tag{10}$$

where $$\hat{f}(t) = \sum_{i=1}^{3} \varphi(t + \hat{p}_i, \hat{p}_i, \hat{\sigma}_i^2) \prod_{j \ne i} \Phi(t + \hat{p}_i, \hat{p}_j, \hat{\sigma}_j^2),$$

if three doses of the test drug are tested; or as $$\hat{\sigma}_T^2 = \int_{-\infty}^{+\infty} t^2 \hat{f}(t)dt - \left( \int_{-\infty}^{+\infty} t\hat{f}(t)dt \right)^2 \tag{12}$$

where $$\hat{f}(t) = \sum_{i=1}^{4} \varphi(t + \hat{p}_i, \hat{p}_i, \hat{\sigma}_i^2) \prod_{j \ne i} \Phi(t + \hat{p}_i, \hat{p}_j, \hat{\sigma}_j^2),$$

if four doses of the test drug are tested, (j) If α 1, estimating the drug effect of the selected dose group using the proportion of success among the remaining $(1-\alpha)N$ in the selected dose group and estimating the variance of this estimate as $$\hat{\sigma}_{aft2} = \hat{p}_{aft}(1 - \hat{p}_{aft})/(1-\alpha)N \tag{3},$$

(k) Estimating the drug effect oat the control group using the proportion of success in the total N patients of the control group and estimating the variance of this estimate as $$\hat{\sigma}_c^2 = \hat{p}_c(1 - \hat{p}_c) \tag{4},$$

(l) Constructing the overall estimate for the drug effect of the selected dose as $$\hat{p}_t = \alpha \hat{p}_s + (1-\alpha) \hat{p}_{aft} - \alpha \hat{b}_{12}(\gamma) \tag{5},$$

(m) Constructing a two-sided 95% confidence interval for the difference of drug effects between the selected dose of the test drug and the control treatment as 95%

$$C.I. = \hat{p}_t - \hat{p}_c \pm 1.96 \sqrt{\alpha^2 \hat{\sigma}_T^2 + (1-\alpha)^2 \hat{\sigma}_{aft}^2 + \hat{\sigma}_c^2}, \tag{6}$$

(n) Calculating p value, the statistical significance of the difference for the drug effects between the selected dose of the test drug and the control treatment as $$\hat{d} = (\hat{p}_t - \hat{p}_c) / \sqrt{\alpha^2 \hat{\sigma}_T^2 + (1-\alpha)^2 \hat{\sigma}_{aft}^2 + \hat{\sigma}_c^2},$$

(o) For equivalence hypothesis, checking whether the confidence interval in step (m) meets the rule specified in step (b); for superiority hypothesis, checking whether the p value of step (n) meets the rule in step (b), (p) Repeating step (e) to step (o) R times, for equivalence hypothesis, calculating the proportion of R runs which meet the rule for equivalence hypothesis, for superiority hypothesis, calculating the proportion of R runs which meet the rule for superiority hypothesis.

5. A method for evaluating drug effect in a multiple dose clinical trial comprising:

(a) Selecting N, the number of patients at the selected dose group by the end of trial and α between 0 and 1, a proportion of N patients per group enrolled by the time of dose selection, (b) Estimating drug effect of each dose group using the average of observations among αN patients in each dose group when they finish their treatment evaluation, (c) Selecting a dose of the test drug which has the highest observed average, (d) Estimating the variances of each dose group as $$\hat{\sigma}_i^2 = \sum_{k=1}^{\alpha N} (x_{ik} - \tilde{x}_i)^2 / \alpha N, \tag{14}$$

(e) Checking homogeneity of variances of drug effect in dose groups by $(1-\beta)100\%$ confidence interval of the ratio of maximum variance versus minimum variance as $$\text{Lower bound} = \frac{\max\{\hat{\sigma}_i^2, i = 1, 2, \cdots, m\}}{\min\{\hat{\sigma}_i^2, i = 1, 2, \cdots, m\}} F_{1-\beta/2}^{-1}(\alpha N - 1, \alpha N - 1) \quad (15)$$

and $$\text{Upper bound} = \frac{\max\{\hat{\sigma}_i^2, i = 1, 2, \cdots, m\}}{\min\{\hat{\sigma}_i^2, i = 1, 2, \cdots, m\}} F_{\beta/2}^{-1}(\alpha N - 1, \alpha N - 1), \quad (16)$$

avoiding using this method if the lower bound or the upper bound exceeds [1/3, 3], wherein β is a positive number between 0 to 1, (f) Estimating the bias between the estimated drug effect and the true drug effect of the selected dose group as $$\hat{b}_{12}(\gamma) = \sqrt{(\hat{\sigma}_1^2 + \hat{\sigma}_2^2)/(2\pi\alpha N)} \, e^{-((i-1)\gamma)^2/2}, \text{ when} \quad (17)$$

$(\bar{x}_1, \bar{x}_2, \hat{\sigma}_1^2, \hat{\sigma}_2^2) \in A_i, i = 1, 2, \ldots$ $$A_i = \left\{ (\bar{x}_1, \bar{x}_2, \hat{\sigma}_1^2, \hat{\sigma}_2^2) \mid (i-1)\gamma \le |\bar{x}_1 - \bar{x}_2| / \sqrt{(\hat{\sigma}_1^2 + \hat{\sigma}_2^2)/\alpha N} < i\gamma \right\} \quad (18)$$

if two doses of the test drug are tested; as $$\hat{b}_{SOC}(\gamma) = \hat{b}_{12}\Phi(0, \bar{x}_3 - \bar{x}_{12}, (\hat{\sigma}_3^2 + \hat{\sigma}_{12}^2)/\alpha N) + \quad (19)$$
$$\hat{b}_{23}\Phi(0, \bar{x}_1 - \bar{x}_{23}, (\hat{\sigma}_1^2 + \hat{\sigma}_{23}^2)/\alpha N) +$$
$$\hat{b}_{31}\Phi(0, \bar{x}_2 - \bar{x}_{31}, (\hat{\sigma}_2^2 + \hat{\sigma}_{31}^2)/\alpha N)$$

if three doses of the test drug are tested; or as $$\hat{b}_{SOC}(\gamma) = \sum_{i \ne j \ne k \ne l} \hat{b}_{ij} \hat{P}(i, j, k, l) \quad (20)$$

where $$\hat{P}(i, j, k, l) = \int_{-\infty}^{\infty} \varphi(u, \bar{x}_{ij}, \hat{\sigma}_{ij}^2/\alpha N) \Phi(u, \bar{x}_k, \hat{\sigma}_k^2/\alpha N) \Phi(u, \bar{x}_l, \hat{\sigma}_l^2/\alpha N) du,$$

if four doses of the test drug are tested, (g) Estimating the variance of $\bar{x}_s - x_s$, the difference between the estimated drug effect and the true drug effect of the selected dose group as $$\hat{\sigma}_T^2 = (\hat{\sigma}_1^2/\alpha N)\Phi(0, \bar{x}_2 - \bar{x}_1, (\hat{\sigma}_1^2 + \hat{\sigma}_2^2)/\alpha N) + \quad (21)$$
$$(\hat{\sigma}_2^2/\alpha N)\Phi(0, \bar{x}_1 - \bar{x}_2, (\hat{\sigma}_1^2 + \hat{\sigma}_2^2)/\alpha N) +$$
$$\frac{(\bar{x}_1 - \bar{x}_2)(\hat{\sigma}_2^2 - \hat{\sigma}_1^2)/\alpha N}{\sqrt{2\pi(\hat{\sigma}_1^2 + \hat{\sigma}_2^2)/\alpha N}} e^{-\frac{(\bar{x}_1 - \bar{x}_2)^2}{2(\hat{\sigma}_1^2 + \hat{\sigma}_2^2)/\alpha N}} -$$
$$\frac{(\hat{\sigma}_2^2 + \hat{\sigma}_1^2)}{2\pi\alpha N} e^{-\frac{(\bar{x}_1 - \bar{x}_2)^2}{(\hat{\sigma}_1^2 + \hat{\sigma}_2^2)/\alpha N}}$$

if two doses of the test drug are tested; as $$\hat{\sigma}_T^2 = \int_{-\infty}^{+\infty} t^2 \hat{f}(t) dt - \left( \int_{-\infty}^{+\infty} t \hat{f}(t) dt \right)^2 \quad (22)$$

where $$\hat{f}(t) = \sum_{i=1}^{3} \varphi(t + \bar{x}_i, \bar{x}_i, \hat{\sigma}_i^2/\alpha N) \prod_{j \ne i} \Phi(t + \bar{x}_i, \bar{x}_j, \hat{\sigma}_j^2/\alpha N)$$

if three doses of the test drug are tested; or as $$\hat{\sigma}_T^2 = \int_{-\infty}^{+\infty} t^2 \hat{f}(t) dt - \left( \int_{-\infty}^{+\infty} t \hat{f}(t) dt \right)^2 \quad (23)$$

where $$\hat{f}(t) = \sum_{i=1}^{4} \varphi(t + \bar{x}_i, \bar{x}_i, \hat{\sigma}_i^2/\alpha N) \prod_{j \ne i} \Phi(t + \bar{x}_i, \bar{x}_j, \hat{\sigma}_j^2/\alpha N),$$

if four doses of the test drug are tested, (h) If a 1, enrolling (1−α)N patients per group in the selected dose group and the control group; otherwise, go to step (j), (i) Estimating the drug effect of the selected dose group using the average of observations in the selected group from the dose selection to the end of clinical trial and estimating the variance of this estimate as $$\hat{\sigma}_{aft}^2 = \sum_{k=1}^{(1-\alpha)N} (x_{sk} - \bar{x}_{aft})^2 / ((1-\alpha)N)^2, \quad (24)$$

(j) Estimating the drug effect of the control group using the average of observations in the total patients of the control group and estimating the variance of this estimate as $$\hat{\sigma}_c^2 = \sum_{k=1}^{N} (y_k - \bar{y})^2 / N^2, \quad (25)$$

(k) Constricting the overall estimate for the drug effect of the selected dose as $$\hat{x}_t = \alpha \bar{x}_s + (1-\alpha) \bar{x}_{aft} - \alpha \hat{b}_{SOC}(\gamma) \quad (26),$$

(l) Constructing a two-sided 95% confidence interval for the difference of drug effects between the selected dose of the test drug and the control treatment as 95%

$$C.I. = \hat{x}_t - \bar{y} \pm 1.96 \sqrt{\alpha^2 \hat{\sigma}_T^2 + (1-\alpha)^2 \hat{\sigma}_{aft}^2 + \hat{\sigma}_c^2}, \quad (27)$$

(m) Calculating p value, the statistical significance of the difference for the drug effects between the selected dose of the test drug and the control treatment as $$p = 1 - \Phi(\hat{d}, 0, 1) + \Phi(-\hat{d}, 0, 1), \text{ where} \quad (28)$$

$$\hat{d} = (\hat{x}_t - \bar{y}) / \sqrt{\alpha^2 \hat{\sigma}_T^2 + (1-\alpha)^2 \hat{\sigma}_{aft}^2 + \hat{\sigma}_c^2},$$

(n) Using the significance level in step (m), the confidence interval in step (l), the overall estimate for the drug effect of the selected dose in step (k), estimate of bias in step (f) or the estimate of the variance of $\bar{x}_s-x_s$ in step (g) to justify the efficacy of the selected dose of the test drug in the New Drug Application of the test drug, (o) Using the significance level in step (m), the confidence interval in step (l), the overall estimate for the drug effect of the selected dose in step (k), estimate of bias in step (f) or the estimate of the variance of $\bar{x}_s-x_s$ in step (g) to justify the efficacy of the selected dose of the test drug in the labeling of the test drug, (p) Using the significance level in step (m), the confidence interval in step (l), the overall estimate for the drug effect of the selected dose in step (k), estimate of bias in step (f) or tie estimate of the variance of $\bar{x}_s-x_s$ in step (g) to justify the efficacy of the selected dose of tie test drug in the advertisement of the test drug.

6. The method of claim 5, wherein drug effect is the mean of a clinical measurement in a dose group, such as average gain of weight in AIDS patients, average reduction of fever, etc.

7. The method of claim 5, wherein doses are different formulations, different strengths, different duration of treatment, or different combinations with other drugs.

8. A method to simulate the probability of the method as described in claim 5 to accept a hypothesis about the drug effect of the test drug comprising:

(a) Presumptively assuming, x, and $\sigma_1^2$, the true mean and variance of the clinical measurement of the drug effect for each treatment group, where the ratio of the maximum to the minimum of variances of dose groups of the test drug is fixed within [1/3, 3], (b) Specifying the rules for the test drug to claim its equivalence or superior to the controlled treatment as such that, for the hypothesis of equivalence, the 95% confidence interval for the difference of the success rates, the test drug's minus the control's, must be no less than $-\Delta$ ($\Delta$ can be any positive number); for the hypothesis of superiority, the p value of the statistical test used must be less than $\epsilon$ ($\epsilon$ is usually chosen as 0.05), (c) Selecting a Repetition Number R (usually ranges from 5,000 to 1,000,000) as appropriate for the level ot reliability of the targeted probability, (d) Selecting N, the number of patients at the selected dose group to be enrolled to the trial, and $\alpha$ between 0 and 1, a proportion of N patients per group enrolled by the time of dose selection, (e) For each group in the clinical trial, generating by computer(s) from a normal distribution, $N(x_1, \sigma_i^2)$, N random numbers as the observed clinical measurements, where $x_1$ and $\sigma_i^2$ are the assumed true mean and variance of clinical measurement for each treatment group in step (a), (f) Estimating drug effect in each dose group using the average of observations in each dose group among the first $\alpha N$ patients in each dose group, (g) Selecting a dose of the test drug which has the highest observed average, (h) Estimating the variances of each dose group as $$\hat{\sigma}_i^2 = \sum_{k=1}^{\alpha N}(x_{ik}-\bar{x}_i)^2/\alpha N, \quad (14)$$

(i) Estimating the bias between the estimated drug effect and the true drug effect of the selected dose group as $$\hat{b}_{12}(\gamma) = \sqrt{(\hat{\sigma}_1^2+\hat{\sigma}_2^2)/(2\pi\alpha N)}\, e^{-((i-1)\gamma)^2/2}, \text{ when} \quad (17)$$

$$(\bar{x}_1, \bar{x}_2, \hat{\sigma}_1^2, \hat{\sigma}_2^2) \in A_i, i=1, 2, \ldots$$

if two doses of the test drug are tested; as $$\hat{b}_{SOC}(\gamma) = \hat{b}_{12}\Phi(0, \bar{x}_3-\bar{x}_{12}, (\hat{\sigma}_3^2+\hat{\sigma}_{12}^2)/\alpha N)+ \quad (19)$$
$$\hat{b}_{23}\Phi(0, \bar{x}_1-\bar{x}_{23}, (\hat{\sigma}_1^2+\hat{\sigma}_{23}^2)/\alpha N)+$$
$$\hat{b}_{31}\Phi(0, \bar{x}_2-\bar{x}_{31}, (\hat{\sigma}_2^2+\hat{\sigma}_{31}^2)/\alpha N)$$

if three doses of the test drug are tested; or as $$\hat{b}_{SOC}(\gamma) = \sum_{i\ne j\ne k\ne l}\hat{b}_{ij}\hat{P}(i,j,k,l) \quad (20)$$

where $$\hat{P}(i,j,k,l) = \int_{-\infty}^{+\infty}\varphi(u, \bar{x}_{ij}, \hat{\sigma}_{ij}^2/\alpha N)\Phi(u, \bar{x}_k, \hat{\sigma}_k^2/\alpha N)\Phi(u, \bar{x}_l, \hat{\sigma}_l^2/\alpha N)du,$$

if four doses of the test drug are tested, (j) Estimating the variance of $\bar{x}_s-x_s$, the difference between the estimated drug effect and the true drug effect of the selected dose group as $$\hat{\sigma}_T^2 = (\hat{\sigma}_1^2/\alpha N)\Phi(0, \bar{x}_2-\bar{x}_1, (\hat{\sigma}_1^2+\hat{\sigma}_2^2)/\alpha N)+ \quad (21)$$
$$(\hat{\sigma}_2^2/\alpha N)\Phi(0, \bar{x}_1-\bar{x}_2, (\hat{\sigma}_1^2+\hat{\sigma}_2^2)/\alpha N)+$$
$$\frac{(\bar{x}_1-\bar{x}_2)(\hat{\sigma}_2^2-\hat{\sigma}_1^2)/\alpha N}{\sqrt{2\pi(\hat{\sigma}_1^2+\hat{\sigma}_2^2)/\alpha N}}e^{-\frac{(\bar{x}_1-\bar{x}_2)^2}{2(\hat{\sigma}_1^2+\hat{\sigma}_2^2)/\alpha N}} -$$
$$\frac{(\hat{\sigma}_2^2+\hat{\sigma}_1^2)}{2\pi\alpha N}e^{-\frac{(\bar{x}_1-\bar{x}_2)^2}{(\hat{\sigma}_1^2+\hat{\sigma}_2^2)/\alpha N}}$$

if two doses of the test drug are tasted; as $$\hat{\sigma}_\tau^2 = \int_{-\infty}^{+\infty}t^2\hat{f}(t)dt - \left(\int_{-\infty}^{+\infty}t\hat{f}(t)dt\right)^2 \quad (22)$$

where $$\hat{f}(t) = \sum_{i=1}^{3}\varphi(t+\bar{x}_i, \bar{x}_i, \hat{\sigma}_i^2/\alpha N)\prod_{j\ne 1}\Phi(t, +\bar{x}_i, \bar{x}_j, \hat{\sigma}_j^2/\alpha N),$$

if three doses of the test drug axe tested; or as $$\hat{\sigma}_i^2 = \int_{-\infty}^{+\infty}t^2\hat{f}(t)dt - \left(\int_{-\infty}^{+\infty}t\hat{f}(t)dt\right)^2 \quad (23)$$

where $$\hat{f}(t) = \sum_{i=1}^{4} \varphi(t + \overline{x}_i, \overline{x}_i, \hat{\sigma}_i^2/\alpha N) \prod_{j \neq 1} \Phi(t, +\overline{x}_i, \overline{x}_j, \hat{\sigma}_j^2/\alpha N), \quad (5)$$

if four doses of the test drug are tested, (k) If α 1, estimating the drug effect of the selected dose group using the average of observations in the selected group among the remaining (1−α)N in the selected dose group and estimating the variance of this estimate as $$\hat{\sigma}_{afi}^2 = \sum_{k=1}^{(1-\alpha)N} (x_{zk} - \overline{x}_{afi})^2 / ((1-\alpha)N)^2, \quad (24)$$

(l) Estimating the drug effect of the control group using the average of observations in the total N patients of the control group and estimating the variance of this estimate as $$\hat{\sigma}_c^2 = \sum_{k=1}^{N} (y_k - \overline{y})^2 / N^2, \quad (25)$$

(m) Constructing the overall estimate for the drug effect of the selected dose as $$\hat{x}_1 = \alpha \overline{x}_s + (1-\alpha)\overline{x}_{afi} - \alpha \hat{b}_{SOC}(\gamma) \quad (26),$$

(n) Constructing a two-sided 95% confidence interval for the difference of drug effects between the selected dose of the test drug and the control treatment as 95%

$$C.I. = \hat{x}_i - \overline{y} \pm 1.96\sqrt{\alpha^2 \hat{\sigma}_T^2 + (1-\alpha)^2 \hat{\sigma}_{afi}^2 + \hat{\sigma}_c^2}, \quad (27)$$

(o) Calculating p value, the statistical significance of the difference for the drug effects between the selected dose of the test drug and the control treatment as $$p = 1 - \Phi(\hat{d}, 0, 1) + \Phi(-\hat{d}, 0, 1), \quad (28)$$

where $\hat{d} = (\hat{x}_i, -\overline{y}) / \sqrt{\alpha^2 \hat{\sigma}_T^2 + (1-\alpha)^2 \hat{\sigma}_{afi}^2 + \hat{\sigma}_c^2}$, (p) For equivalence hypothesis, checking whether the confidence interval in step (n) meets the rule specified in step (b); for superiority hypothesis, checking whether the p value of step (o) meets the rule in step (b), (q) Repeating step (e) to step (p) R times, for equivalence hypothesis, calculating the proportion of R runs which meet the rule for equivalence hypothesis, for superiority hypothesis, calculating the proportion of R runs which meet the rule for superiority hypothesis.

9. A computer software performing claim 1, claim 5, claim 4 or claim 8.

* * * * *

UNITED STATES PATENT AND TRADEMARK OFFICE
CERTIFICATE OF CORRECTION

PATENT NO : 6,041,788
DATED : March 28, 2000
INVENTOR(S): Liji Shen.

Page 1 of 7

It is certified that error appears in the above-identified patent and that said Letters Patent is hereby corrected as shown below:

Col. 4, line 51, change "$\alpha\ 1$" to ---$\alpha \neq 1$---.

Col. 4, line 55, after "selected dose group by", delete "$\hat{\sigma}^2_{afi}=$".

Col. 4, line 62, change "$\hat{\sigma}^2_c = \hat{p}_c(1-\hat{p}_c)/N$" to

--- $$\hat{\sigma}^2_c = \hat{p}_c(1-\hat{p}_c)/N \qquad (4)$$ ---

Col. 4, line 65, change "$\hat{p}_l \alpha \hat{p}_s (1-\alpha) \hat{p}_{afi} - \alpha \hat{b}_{12}(\gamma),$" to --- $\hat{p}_l = \alpha \hat{p}_s + (1-\alpha) \hat{p}_{afi} - \alpha \hat{b}_{12}(\gamma)$, ---

Col. 4, line 66, change "the variance of $\hat{p}_1$ by" to ---the variance of $\hat{p}_l$ by---.

Col. 6, line 8 to 9, change
"$f(t) = \varphi(t+p_1,p_1,\sigma_1^2)\Phi(t+p_1,p_2,\sigma_2^2)\varphi(t+p_2,p_2,\sigma_2^2)\Phi(t+p_2,p_1,\sigma_1^2)$" to
--- $f(t) = \varphi(t+p_1,p_1,\sigma_1^2)\Phi(t+p_1,p_2,\sigma_2^2) + \varphi(t+p_2,p_2,\sigma_2^2)\Phi(t+p_2,p_1,\sigma_1^2)$ ---

Col. 6, line 17, change "$\hat{p}_s - p\hat{s}$" to --- $\hat{p}_s - p_{\hat{s}}$ ---.

Col. 6, line 48, change "Remember that $\hat{p}_1$" to ---Remember that $\hat{p}_l$---.

UNITED STATES PATENT AND TRADEMARK OFFICE
CERTIFICATE OF CORRECTION

PATENT NO : 6,041,788
DATED : March 28, 2000
INVENTOR(S): Liji Shen

It is certified that error appears in the above-identified patent and that said Letters Patent is hereby corrected as shown below:

Col. 12 line 38 to 50, Change

"$\hat{b}_{SOC}(\gamma) = \hat{b}_{12}\Phi(0,$ $\hat{p}_3 - \hat{p}_{12},$ $\hat{\sigma}_3^2 + \hat{\sigma}_{12}^2) +$ $\hat{b}_{23}\Phi(0, \hat{p}_1 -$ $\hat{p}_{23}, \hat{\sigma}_1^2 + \hat{\sigma}_{23}^2) +$ $\hat{b}_{31}\Phi(0, \hat{p}_2 - \hat{p}_{31},$ $\hat{\sigma}_2^2 + \hat{\sigma}_{31}^2)$ (9)"

to $$--\hat{b}_{SOC}(\gamma) = \hat{b}_{12}\Phi(0, \hat{p}_3 - \hat{p}_{12}, \hat{\sigma}_3^2 + \hat{\sigma}_{12}^2) +$$
$$\hat{b}_{23}\Phi(0, \hat{p}_1 - \hat{p}_{23}, \hat{\sigma}_1^2 + \hat{\sigma}_{23}^2) +$$
$$\hat{b}_{31}\Phi(0, \hat{p}_2 - \hat{p}_{31}, \hat{\sigma}_2^2 + \hat{\sigma}_{31}^2) \quad (9)--$$

Col. 17, line 47, change "That is, $x_{\bar{s}} = x_i$ if $\bar{x}_s = \bar{s}_i$." to
---That is, $$x_{\bar{s}} = x_i \text{ if } \bar{x}_s = \bar{x}_i \quad (13)--.$$

Col. 17, line 52, change "$\hat{\sigma}_i^2 = (\sum(x_{ik} - \bar{x}_i))^2 / \alpha N$" to $$--\hat{\sigma}_i^2 = \sum_{k=1}^{\alpha N}(x_{ik} - \bar{x}_i)^2 / \alpha N \quad (14)--.$$

UNITED STATES PATENT AND TRADEMARK OFFICE
CERTIFICATE OF CORRECTION

PATENT NO : 6,041,788
DATED : March 28, 2000
INVENTOR(S): Liji Shen

It is certified that error appears in the above-identified patent and that said Letters Patent is hereby corrected as shown below:

Col. 18, line 27 to 37, change

"$\hat{b}_{SOC}(\gamma) = \hat{b}_{12}\Phi(0,$ $\bar{x}_3 - \bar{x}_{12}, (\hat{\sigma}_3^2 +$ $\hat{\sigma}_{12}^2)/\alpha N) + \hat{b}_{23}\Phi(0,$ $\bar{x}_1 - \bar{x}_{23}, (\hat{\sigma}_1^2 + \hat{\sigma}_{23}^2)/\alpha N) +$ $+\hat{b}_{31}\Phi(0,\bar{x}_2$ $-\bar{x}_{31},(\hat{\sigma}_2^2 + \hat{\sigma}_{31}^2)/\alpha N)$ (19)"

to $--\hat{b}_{SOC}(\gamma) = \hat{b}_{12}\Phi(0,\bar{x}_3 - \bar{x}_{12},(\hat{\sigma}_3^2 + \hat{\sigma}_{12}^2)/\alpha N) +$
$\hat{b}_{23}\Phi(0,\bar{x}_1 - \bar{x}_{23},(\hat{\sigma}_1^2 + \hat{\sigma}_{23}^2)/\alpha N) +$
$\hat{b}_{31}\Phi(0,\bar{x}_2 - \bar{x}_{31},(\hat{\sigma}_2^2 + \hat{\sigma}_{31}^2)/\alpha N)$ (19)--

Col. 19, line 29, change "$\alpha$ 1" to ---$\alpha \neq 1$---.

Col. 19, line 55, change " $\hat{x}_1 = \alpha\bar{x}_s + (1-\alpha)\bar{x}_{aft} - \alpha\hat{b}_{SOC}(\gamma)$ (26)," to --- $\hat{x}_i = \alpha\bar{x}_s + (1-\alpha)\bar{x}_{aft} - \alpha\hat{b}_{SOC}(\gamma)$ (26)---.

Col. 19 line 56, change "the variance of $\hat{x}$, by" to ---the variance of $\hat{x}_i$ by---.

Col. 25, line 45, "$\alpha$ between 0 aid 1" to ---$\alpha$ between 0 and 1---.

UNITED STATES PATENT AND TRADEMARK OFFICE
CERTIFICATE OF CORRECTION

PATENT NO : 6,041,788
DATED : March 28, 2000
INVENTOR(S): Liji Shen

Page 4 of 7

It is certified that error appears in the above-identified patent and that said Letters Patent is hereby corrected as shown below:

Col. 27, line 16, change "$\hat{f}(t) = \sum_{i=1}^{3} \varphi(t + \hat{p}_1, \hat{p}_1, \hat{\sigma}_1^2) \prod_{j \neq i} \Phi(t + \hat{p}_1, \hat{p}_j, \hat{\sigma}_j^2)$" to --- $\hat{f}(t) = \sum_{i=1}^{3} \varphi(t + \hat{p}_i, \hat{p}_i, \hat{\sigma}_i^2) \prod_{j \neq i} \Phi(t + \hat{p}_i, \hat{p}_j, \hat{\sigma}_j^2)$ ---

Col. 27, line 22, change "$\hat{\sigma}_Y^2 = \int_{-\infty}^{\infty} t^2 \hat{f}(t) dt - (\int_{-\infty}^{\infty} t \hat{f}(t) dt)^2$" to --- $\hat{\sigma}_T^2 = \int_{-\infty}^{\infty} t^2 \hat{f}(t) dt - (\int_{-\infty}^{\infty} t \hat{f}(t) dt)^2$ ---

Col. 27, line 30, change "$\hat{f}(t) = \sum_{i=1}^{\alpha} \varphi(t + \hat{p}_1, \hat{p}_1, \hat{\sigma}_i^2) \prod_{j \neq i} \Phi(t + \hat{p}_1, \hat{p}_j, \hat{\sigma}_j^2)$" to --- $\hat{f}(t) = \sum_{i=1}^{4} \varphi(t + \hat{p}_i, \hat{p}_i, \hat{\sigma}_i^2) \prod_{j \neq i} \Phi(t + \hat{p}_i, \hat{p}_j, \hat{\sigma}_j^2)$ ---

Col. 27, line 35, change "$\alpha\ 1$" to --- $\alpha \neq 1$ ---.

Col. 27, line 44, change "$\hat{\sigma}_{aft}^2 \hat{p}_{aft}(1 \hat{p}_{aft}) / (1 - \alpha)N$" to --- $\hat{\sigma}_{aft}^2 = \hat{p}_{aft}(1 - \hat{p}_{aft}) / (1 - \alpha)N$ ---.

Col. 27, line 55, change "$\hat{p} = \alpha \hat{p}_s + (1-\alpha) \hat{p}_{aft} - \alpha \hat{b}_{12}(\gamma)$" to --- $\hat{p}_t = \alpha \hat{p}_s + (1-\alpha) \hat{p}_{aft} - \alpha \hat{b}_{12}(\gamma)$ ---.

UNITED STATES PATENT AND TRADEMARK OFFICE
CERTIFICATE OF CORRECTION

PATENT NO : 6,041,788
DATED : March 28, 2000
INVENTOR(S): Liji Shen

It is certified that error appears in the above-identified patent and that said Letters Patent is hereby corrected as shown below:

Col. 28, line 37 change "the true rate of success, $p_1$" to
--- the true rate of success, $p_i$ ---.

Col. 28, line 64, change "(g) Selecting a dose of tie test drug" to
---(g) Selecting a dose of the test drug---.

Col. 30, line 1, change "$\alpha \ 1$" to ---$\alpha \neq 1$---.

Col. 30, line 5, change "$\hat{\sigma}_{aft\,2} =$" to --- $\hat{\sigma}^2_{aft} =$ ---.

Col. 30 line 13, change "$\hat{\sigma}_c^2 = \hat{p}_c(1 - \hat{p}_c)$" to --- $\hat{\sigma}_c^2 = \hat{p}_c(1 - \hat{p}_c)/N$ ---.

Col. 30, line 18, change "$\hat{p}_1 = \alpha \hat{p}_s + (1-\alpha)\hat{p}_{aft} - \alpha \hat{b}_{12}(\gamma)$" to
--- $\hat{p}_t = \alpha \hat{p}_s + (1-\alpha)\hat{p}_{aft} - \alpha \hat{b}_{12}(\gamma)$ ---.

Col 30, line 30, after "dose of the test drug and the control treatment as" insert
--- $p = 1 - \Phi(\hat{d},0,1) + \Phi(-\hat{d},0,1)$ ---.

Col. 32, line 21, change "If $\alpha \ 1$" to ---If $\alpha \neq 1$---.

Col. 32, line 45, change "$\hat{x}_1 = \alpha \bar{x}_s + (1-\alpha)\bar{x}_{aft} - \alpha \hat{b}_{SOC}(\gamma)$" to
--- $\hat{x}_t = \alpha \bar{x}_s + (1-\alpha)\bar{x}_{aft} - \alpha \hat{b}_{SOC}(\gamma)$ ---.

UNITED STATES PATENT AND TRADEMARK OFFICE
CERTIFICATE OF CORRECTION

PATENT NO : 6,041,788
DATED : March 28, 2000
INVENTOR(S): Liji Shen

It is certified that error appears in the above-identified patent and that said Letters Patent is hereby corrected as shown below:

Col. 33, line 26, change "Presumptively assuming, x and $\sigma_1^2$," to ---Presumptively assuming, $x_i$ and $\sigma_i^2$,---.

Col. 33, line 42, change "the level ot reliability" to ---the level of reliability---.

Col. 33, line 49, change "N($x_1, \sigma_i^2$)" to ---N($x_i, \sigma_i^2$)---.

Col. 33, line 51, change "where $x_1$ and $\sigma_i^2$" to ---where $x_i$ and $\sigma_i^2$---.

Col. 34, line 65, change "$\hat{\sigma}_i^2 = \int_{-\infty}^{\infty} t^2 \hat{f}(t)dt - (\int_{-\infty}^{\infty} t \hat{f}(t)dt)^2$" to ---$\hat{\sigma}_T^2 = \int_{-\infty}^{\infty} t^2 \hat{f}(t)dt - (\int_{-\infty}^{\infty} t \hat{f}(t)dt)^2$---.

Col. 35, line 8, change "If α 1" to ---If α≠1---.

Col. 35, line 15, change "$\hat{\sigma}_{aft}^2 = \sum_{k=1}^{(1-\alpha)N}(x_{zk} - \bar{x}_{aft})^2 /((1-\alpha)N)^2$" to ---$\hat{\sigma}_{aft}^2 = \sum_{k=1}^{(1-\alpha)N}(x_{sk} - \bar{x}_{aft})^2 /((1-\alpha)N)^2$---.

Col. 35, line 31, change "$\hat{x}_1 = \alpha\bar{x}_s + (1-\alpha)\bar{x}_{aft} - \alpha\hat{b}_{SOC}(\gamma)$" to ---$\hat{x}_t = \alpha\bar{x}_s + (1-\alpha)\bar{x}_{aft} - \alpha\hat{b}_{SOC}(\gamma)$---

UNITED STATES PATENT AND TRADEMARK OFFICE
CERTIFICATE OF CORRECTION

PATENT NO : 6,041,788
DATED : March 28, 2000
INVENTOR(S): Liji Shen

It is certified that error appears in the above-identified patent and that said Letters Patent are hereby corrected as shown below:

Col. 36, line 5, change "$\hat{x}_i - \bar{y} \pm 1.96\sqrt{\alpha^2 \hat{\sigma}_T^2 + (1-\alpha)^2 \hat{\sigma}_{aft}^2 + \hat{\sigma}_c^2}$" to
--- $\hat{x}_t - \bar{y} \pm 1.96\sqrt{\alpha^2 \hat{\sigma}_T^2 + (1-\alpha)^2 \hat{\sigma}_{aft}^2 + \hat{\sigma}_c^2}$ ---.

Col. 36, line 15, change "$\hat{d} = (\hat{x}_t, -\bar{y})/\sqrt{\alpha^2 \hat{\sigma}_T^2 + (1-\alpha)^2 \hat{\sigma}_{aft}^2 + \hat{\sigma}_c^2}$" to
--- $\hat{d} = (\hat{x}_t - \bar{y})/\sqrt{\alpha^2 \hat{\sigma}_T^2 + (1-\alpha)^2 \hat{\sigma}_{aft}^2 + \hat{\sigma}_c^2}$ ---.

Signed and Sealed this

Twentieth Day of February, 2001

Attest:

NICHOLAS P. GODICI

Attesting Officer

Acting Director of the United States Patent and Trademark Office